United States Patent [19]
Gustafsson et al.

[11] Patent Number: 5,965,692
[45] Date of Patent: Oct. 12, 1999

[54] PRODRUGS OF THROMBIN INHIBITORS

[75] Inventors: David Gustafsson, Kullavik; Jan-Erik Nyström, Lindome; Henrik Sörensen, Mölnlycke; Mikael Sellén, Göteborg, all of Sweden

[73] Assignee: Astra AB, Sodertalje, Sweden

[21] Appl. No.: 08/776,231

[22] PCT Filed: Dec. 17, 1996

[86] PCT No.: PCT/SE96/01680

§ 371 Date: Jan. 31, 1997

§ 102(e) Date: Jan. 31, 1997

[87] PCT Pub. No.: WO97/23499

PCT Pub. Date: Jul. 3, 1997

[30] Foreign Application Priority Data

Dec. 21, 1995 [GB] United Kingdom ............ 9526273
Feb. 15, 1996 [SE] Sweden ........................... 9600556

[51] Int. Cl.⁶ .............. A61K 38/00; A61K 38/06; C07K 5/00; C07K 7/00
[52] U.S. Cl. .............. 530/300; 530/331; 514/18; 514/19; 548/535
[58] Field of Search ............ 514/18, 19; 530/300, 530/331; 548/535

[56] References Cited

U.S. PATENT DOCUMENTS

| | | |
|---|---|---|
| 4,346,078 | 8/1982 | Bajusz et al. |
| 4,568,636 | 2/1986 | Svendsen |
| 4,703,036 | 10/1987 | Bajusz et al. |
| 4,977,168 | 12/1990 | Bernat et al. |
| 5,037,819 | 8/1991 | Han |
| 5,110,812 | 5/1992 | Han |
| 5,187,157 | 2/1993 | Kettner et al. |
| 5,260,307 | 11/1993 | Ackermann et al. |
| 5,273,982 | 12/1993 | Alig et al. |
| 5,561,146 | 10/1996 | Kim et al. |
| 5,583,146 | 12/1996 | Kimball et al. |
| 5,602,253 | 2/1997 | Antonsson et al. |
| 5,614,499 | 3/1997 | Bylund et al. ............ 514/19 |
| 5,629,324 | 5/1997 | Vacca et al. ............ 514/316 |
| 5,705,487 | 1/1998 | Schacht et al. |
| 5,707,966 | 1/1998 | Schacht et al. |
| 5,710,130 | 1/1998 | Schacht et al. |
| 5,726,159 | 3/1998 | Schacht et al. |
| 5,744,487 | 4/1998 | Ohshima et al. ......... 514/326 |
| 5,786,383 | 7/1998 | Clement ................... 514/633 |

FOREIGN PATENT DOCUMENTS

| | | |
|---|---|---|
| 0 074 787 | 3/1983 | European Pat. Off. |
| 0 192 135 | 3/1986 | European Pat. Off. |
| 0 185 390 | 6/1986 | European Pat. Off. |
| 0 195 212 | 9/1986 | European Pat. Off. |
| 0 235 692 | 9/1987 | European Pat. Off. |
| 0 293 881 A2 | 12/1988 | European Pat. Off. |
| 0 362 002 | 4/1990 | European Pat. Off. |
| 0 364 344 A2 | 4/1990 | European Pat. Off. |
| 0 364 344 A3 | 4/1990 | European Pat. Off. |
| 0 468 231 A2 | 1/1991 | European Pat. Off. |
| 0 479 489 | 9/1991 | European Pat. Off. |
| 0 468 231 A3 | 1/1992 | European Pat. Off. |
| 0 471 651 | 2/1992 | European Pat. Off. |
| 0 513 543 | 11/1992 | European Pat. Off. |
| 0 526 877 A2 | 2/1993 | European Pat. Off. |
| 0 526 877 A3 | 2/1993 | European Pat. Off. |
| 0 530 167 A1 | 3/1993 | European Pat. Off. |
| 0 542 525 A2 | 5/1993 | European Pat. Off. |
| 0 559 046 A1 | 9/1993 | European Pat. Off. |
| 0 601 459 A2 | 6/1994 | European Pat. Off. |
| 0 641 779 A1 | 3/1995 | European Pat. Off. |
| 0 648 780 A1 | 4/1995 | European Pat. Off. |
| 0 669 317 A1 | 8/1995 | European Pat. Off. |
| 0 686 642 A2 | 12/1995 | European Pat. Off. |
| 2 085 444 | 4/1982 | United Kingdom |
| 9 204 371 | 3/1992 | WIPO |
| 9 208 709 | 3/1992 | WIPO |
| 9 207 869 | 5/1992 | WIPO |
| WO 93/11152 | 6/1993 | WIPO |
| WO 93/18060 | 9/1993 | WIPO |
| WO 94/29336 | 12/1994 | WIPO |
| WO 95/01168 | 1/1995 | WIPO |
| WO 95/23609 | 9/1995 | WIPO |
| WO 95/35309 | 12/1995 | WIPO |
| WO 96/14084 | 5/1996 | WIPO |
| WO 96/16671 | 6/1996 | WIPO |
| WO 96/25426 | 8/1996 | WIPO |
| WO 96/31504 | 10/1996 | WIPO |
| WO 96/32110 | 10/1996 | WIPO |

OTHER PUBLICATIONS

Boykin et al, "Anti–Pneumocystis Activity of Bis–Amidoximes and Bis–O–Alkylamidoximes Prodrugs", Bioorganic & Medicinal Chemistry Letters 6(24):3017–3020 (1996).

Taylor, "Improved passive oral drug delivery via prodrugs", Advanced Drug Delivery Reviews 19;131–148 (1996).

Hauptmann et al., "Reduction of a benzamidoxime derivative to the corresponding benzamidine in vivo and in vitro", Pharmazie 43:559 (1988).

Tatsumi and Ishigai, "Oxime–Metabolizing Activity of Liver Aldehyde Oxidase", Archives of Biochemistry and Biophysics 253(2):413–418 (1987).

Stewart et al, "Solid Phase Peptide Synthesis," Pierce Chemical Co., pp. 18–20 (w/appendix).

(List continued on next page.)

*Primary Examiner*—Avis M. Davenport
*Attorney, Agent, or Firm*—Nixon & Vanderhye

[57] ABSTRACT

There is provided compounds of formula I, $$R^1O(O)C\text{---}CH_2\text{---}(R)Cgl\text{-Aze-Pab-}R^2 \qquad I$$

wherein $R^1$ and $R^2$ have meanings given in the description, which are useful as prodrugs of inhibitors of trypsin-like proteases, such as thrombin, and in particular in the treatment of conditions where inhibition of thrombin is required (eg thrombosis) or as anticoagulants.

38 Claims, No Drawings

OTHER PUBLICATIONS

Bajusz, "Interaction of Trypsin–like Enzymes with Small Inhibitors," Symposia Biologica Hungarica 25, pp. 277–298, (1984).

Jackson et al, "Pharmacological Assessment of the Antithrombotic Activity . . . ," J. of Pharm. Exp. Ther., vol. 261, pp. 546–552 (1992).

Knabb et al, "In Vivo Characterization of New Synthetic Thrombin Inhibitor," Thrombosis and Haemostasis, vol. 67, No. 1, pp. 56–59 (1992).

Bajusz et al. "Inhibition of Thrombin with H–and Boc–D––Phe–Pro–Agm," Chem. Abs. 99: 205609w (1993).

Klement et al, "The Effect of Thrombin Inhibitors on Tissue Plasminogen . . . ," Thrombosis and Haemostasis, vol. 68, No. 1, pp. 64–68 (1992).

Märki et al, "The Anticoagulant and Antithrombotic Properties of Hirudins," Thormsos and Haemostasis, vol. 64, No. 3, pp. 344–348 (1990).

Broersma et al, "The Effect of Thrombin Induction Inhibition in a Rat Arterial Thrombosis Model," Thrombisis Research, vol. 64, pp. 405–412 (1991).

Persson et al, Thorax, vol. 47, pp. 993–1000 (1992).

Salomonson et al, Am. Rev. Resp. Dis., vol. 146, pp. 1535–1542 (1992).

Markwardt et al, Biochem. Pharm., vol. 23, pp. 2247–2256 (1974).

Malek et al, "Palladium–catalyzed synthesis of Cinnamylamides," J. Org. Chem., vol. 47, No. 27, pp. 5395–5397 (1982).

Malek et al, Chem. Abs. 98: 16353 (1983).

Chung et al, J. Organic Chem., vol. 1, pp. 270–275.

Glusa et al, "The influence of benzamidine derivatives on human platelet function," Thrombosis et Diathesis Haemorrhagica, vol. 31, pp. 172–178 (1974).

Anderson and Lok, J. Organic Chem., vol. 37, p. 3953 (1972).

Fareed et al, Ann. N.Y. Acad. Sci., vol. 370, pp. 765–784 (1981).

Geratz, J.D., "Inhibition of thrombin, plasmin and plasminogen compounds," Thrombosis et Diathesis Halmorrhagica, vol. 23, No. 3, pp. 486–499 (1970).

PRODRUGS OF THROMBIN INHIBITORS

FIELD OF THE INVENTION

This invention relates to pharmaceutically useful prodrugs of pharmaceutically active compounds, which active compounds are, in particular, competitive inhibitors of trypsin-like serine proteases, especially thrombin, the use of the prodrugs as medicaments, pharmaceutical compositions containing them and synthetic routes to their production.

BACKGROUND

Blood coagulation is the key process involved in both haemostasis (ie the prevention of blood loss from a damaged vessel) and thrombosis (ie the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would therefore be expected to exhibit antithrombotic activity. In addition, antithrombotic activity would be expected to be enhanced by effective inhibition of the positive feedback mechanism.

PRIOR ART

The development of low molecular weight inhibitors of thrombin has been described by Claesson in Blood Coagul. Fibrin. (1994) 5, 411.

Blomback et al (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg would be the most effective inhibitor.

Low molecular weight peptide-based thrombin inhibitors have subsequently been disclosed in, for example, U.S. Pat. No. 4,346,078; International Patent Applications WO 93/11152, WO 94/29336, WO 93/18060 and WO 95/01168; and European Patent Applications 648 780, 468 231, 559 046, 641 779, 185 390, 526 877, 542 525, 195 212, 362 002, 364 344, 530 167, 293 881, 686 642 and 601 459.

More recently, thrombin inhibitors based on peptide derivatives have been disclosed in European Patent Application 0 669 317 and International Patent Applications WO 95/23609, WO 95/35309, WO 96/25426 and WO 94/29336.

In particular, the latter application discloses the peptide derivatives R$^a$OOC—CH$_2$—(R)Cgl-Aze-Pab-H, wherein R$^a$ represents H, benzyl or C$_{1-6}$ alkyl.

Although these active compounds are known to exhibit significant antithrombin activity, it would be beneficial to improve their pharmacokinetic properties both after oral and parenteral administration. Examples of pharmacokinetic properties which it is desirable to improve include:

(a) providing an improved absorption from the gastrointestinal tract, with a view to reducing intra- and/or inter-individual variability in relation to the bioavailability of the active compounds;

(b) flattening the plasma concentration time profile (ie reducing the peak/trough ratio in the plasma concentration over the dosing interval), with a view to reducing the risk of falling outside the therapeutic interval and the side effects caused by a concentration peak which is too high (eg bleeding), and those caused by one which is too low (eg thrombus formation); and (c) increasing the duration of action of the active compounds.

Moreover, oral and parenteral administration of active thrombin inhibitors may lead to undesirable local bleeding (eg in the intestinal lumen or subcutaneously) as a result of a high local concentration, Finally, orally administered active thrombin inhibitors which also inhibit trypsin and other serine proteases in the gastrointestinal tract may exhibit additional side effects, including indigestion (eg if trypsin is inhibited in the intestinal lumen).

Although certain N-benzyloxycarbonyl derivatives of the aforementioned active compounds are also disclosed as thrombin inhibitors in International Patent Application WO 94/29336, that these derivatives may be useful as prodrugs is not mentioned. In fact, WO 94/29336 makes no mention of suitable prodrugs of the active compounds.

We have found that the above problems may be solved by administering compounds according to the present invention which, whilst inactive per se, upon oral and/or parenteral administration are metabolised in the body to form active thrombin inhibitors, including those mentioned above.

DISCLOSURE OF THE INVENTION

According to the invention there is provided a compound of formula I,

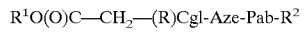

$$R^1O(O)C—CH_2—(R)Cgl\text{-}Aze\text{-}Pab\text{-}R^2 \qquad I$$

wherein

R$^1$ represents —R$^3$ or —A$^1$C(O)N(R$^4$)R$^5$ or —A$^1$C(O)OR$^4$;

A$^1$ represents C$_{1-5}$ alkylene;

R$^2$ (which replaces one of the hydrogen atoms in the amidino unit of Pab-H) represents OH, OC(O)R$^6$, C(O)OR$^7$ or C(O)OCH(R$^8$)OC(O)R$^9$;

R$^3$ represents H, C$_{1-10}$ alkyl, or C$_{1-3}$ alkylphenyl (which latter group is optionally substituted by C$_{1-6}$ alkyl, C$_{1-6}$ alkoxy, nitro or halogen);

R$^4$ and R$^5$ independently represent H, C$_{1-6}$ alkyl, phenyl, 2-naphthyl or, when R$_1$ represents —A$^1$C(O)N(R$^4$)R$^5$, together with the nitrogen atom to which they are attached represent pyrrolidinyl or piperidinyl;

R$^6$ represents C$_{1-17}$ alkyl, phenyl or 2-naphthyl (all of which are optionally substituted by C$_{1-6}$ alkyl or halogen);

R$^7$ represents 2-naphthyl, phenyl, C$_{1-3}$ alkylphenyl (which latter three groups are optionally substituted by C$_{1-6}$ alkyl, C$_{1-6}$ alkoxy, nitro or halogen), or C$_{1-12}$ alkyl (which latter group is optionally substituted by C$_{1-6}$ alkoxy, C$_{1-6}$ acyloxy or halogen);

R$^8$ represents H or C$_{1-4}$ alkyl; and

R$^9$ represents 2-naphthyl, phenyl, C$_{1-6}$ alkoxy or C$_{1-8}$ alkyl (which latter group is optionally substituted by halogen, C$_{1-6}$ alkoxy or C$_{1-6}$ acyloxy); provided that when R$^1$ represents R$^3$, R$^3$ represents benzyl, methyl, ethyl, n-butyl or n-hexyl and $R^2$ represents $C(O)OR^7$, then $R^7$ does not represent benzyl;

or a pharmaceutically-acceptable salt thereof (hereinafter referred to as "the compounds of the invention").

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. All diastereoisomers may be separated using conventional techniques, eg chromatography or fractional crystallisation. The various stereoisomers may be isolated by separation of a racemic or other mixture of the compounds using conventional, eg fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (eg HPLC, chromatography over silica). All stereoisomers are included within the scope of the invention.

According to a further aspect of the invention there is provided the use of a compound of formula I, as hereinbefore defined but without the proviso, as a prodrug.

Alkyl groups which $R^3$, $R^4$, $R^5$, $R^6$, $R^7$ and $R^9$ may represent may be linear or, when there are a sufficient number of carbon atoms, be branched, be cyclic or partially cyclic, be saturated or unsaturated, be interrupted by oxygen and/or be substituted or terminated by OH, provided that the OH group is not attached to an $sp^2$ carbon atom or a carbon atom which is adjacent to an oxygen atom.

By "partially cyclic alkyl groups" we mean groups such as $CH_2Ch$.

Alkyl groups which $R^8$ may represent, and $R^3$, $R^6$ and $R^7$ may be substituted by, may be linear or, when there are a sufficient number of carbon atoms, be branched, be saturated or unsaturated and/or be interrupted by oxygen.

The alkyl portion of alkylphenyl groups which $R^3$ and $R^7$ may represent may be linear or, when there are a sufficient number of carbon atoms, be branched and/or be saturated or unsaturated.

Alkylene groups which $A^1$ may represent may be linear or, when there are a sufficient number of carbon atoms, be branched and/or be saturated or unsaturated.

Alkoxy groups which $R^9$ may represent, and $R^3$, $R^7$ and $R^9$ may be substituted by, may be linear or, when there are a sufficient number of carbon atoms, be branched and/or be saturated or unsaturated.

Acyloxy groups which $R^7$ and $R^9$ may be substituted by may be linear or, when there are a sufficient number of carbon atoms, be branched and/or be saturated or unsaturated.

Abbreviations are listed at the end of this specification.

According to a further aspect of the invention there is provided a compound of formula I, as hereinbefore defined, with the additional provisos that:

(a) $R^1$ does not represent $-A^1C(O)OR^4$;

(b) $R^4$ and $R^5$ do not independently represent H;

(c) $R^6$ does not represent $C_{1-17}$ alkyl, when $R^2$ represents $OC(O)R^6$.

According to a further aspect of the invention there is provided a compound of formula I, wherein:

(a) $R^1$ represents $-A^1C(O)OR^4$;

(b) $R^4$ and $R^5$ independently represent H;

(c) $R^6$ represents $C_{1-17}$ alkyl, when $R^2$ represents $OC(O)R^6$.

When $R^1$ represents $-A^1C(O)N(R^4)R^5$, preferred compounds of the invention include those wherein:

$A^1$ represents $C_{1-3}$ alkylene;

$R^4$ represents H or $C_{1-6}$ alkyl;

$R^5$ represents $C_{1-6}$ alkyl or $C_{4-6}$ cycloalkyl; or those wherein $R^4$ and $R_5$ together represent pyrrolidinyl.

When $R^1$ represents $-A^1C(O)OR^4$, preferred compounds of the invention include those wherein:

$A^1$ represents $C_{1-5}$ alkylene;

$R^4$ represents $C_{1-6}$ alkyl.

When $R^1$ represents $R^3$, preferred compounds of the invention include those wherein $R^3$ represents H, $C_{1-10}$ alkyl (which latter group may be linear or, when there are a sufficient number of carbon atoms, may be branched and/or be partially cyclic or cyclic), or $C_{1-3}$ alkylphenyl (which latter groups is optionally substituted, may be linear or, when there are a sufficient number of carbon atoms, be branched).

Preferred compounds of the invention include those wherein $R^2$ represents OH, $OC(O)R^6$ (wherein, in the latter case, $R^6$ represents optionally substituted phenyl or $C_{1-17}$ alkyl (which latter group may be linear or, when there are a sufficient number of carbon atoms, may be branched, be cyclic or partially cyclic, and/or be saturated or unsaturated)), $C(O)OR^7$ (wherein, in the latter case, $R^7$ represents optionally substituted phenyl, $C_{1-12}$ alkyl (which latter group is optionally substituted, may be linear or, when there are a sufficient number of carbon atoms, may be branched, cyclic or partially cyclic, and/or saturated or unsaturated), or $C_{1-3}$ alkylphenyl (which latter group is optionally substituted, may be linear or, when there are a sufficient number of carbon atoms, may be branched)), or $C(O)OCH(R^8)OC(O)R^9$ (wherein, in the latter case, $R^8$ represents H or methyl, and $R^9$ represents phenyl, or $C^{1-8}$ alkyl (which latter group is optionally substituted, may be linear or, when there are a sufficient number of carbon atoms, may be branched and/or cyclic or partially cyclic)).

More preferred compounds of the invention include those wherein:

$R^1$ represents H, linear $C_{1-10}$ alkyl, branched $C_{3-10}$ alkyl, partially cyclic $C_{4-10}$ alkyl, $C_{4-10}$ cycloalkyl, optionally substituted linear $C_{1-3}$ alkylphenyl, optionally substituted branched $C_3$ alkylphenyl, $-A^1C(O)N(R^4)R^5$ (wherein, in the latter case, $A^1$ represents $C_{1-3}$ alkylene, and $R^4$ represents H or $C_{1-3}$ alkyl and $R^5$ represents $C_{2-6}$ alkyl or $C_{5-6}$ cycloalkyl, or $R^4$ and $R^5$ together represent pyrrolidinyl), or $-A^1C(O)OR^4$ (wherein, in the latter case, $A^1$ represents $C_{1-5}$ alkylene and $R^4$ represents $C_{1-4}$ alkyl);

$R^2$ represents OH, $OC(O)R^6$ (wherein, in the latter case, $R^6$ represents optionally substituted phenyl, linear $C_{1-4}$ alkyl, branched $C_{3-4}$ alkyl or cis-oleyl), $C(O)OR^7$ (wherein, in the latter case, $R^7$ represents optionally substituted and/or optionally unsaturated linear $C_{1-4}$ alkyl or optionally substituted and/or optionally unsaturated branched $C_{3-4}$ alkyl, optionally substituted phenyl, or optionally substituted linear $C_{1-3}$ alkylphenyl or optionally substituted branched $C_3$ alkylphenyl) or $C(O)OCH(R^8)OC(O)R^9$ (wherein, in the latter case, $R^8$ represents H or methyl and $R^9$ represents phenyl, $C_{5-7}$ cycloalkyl, linear $C_{1-6}$ alkyl, branched $C_{3-6}$ alkyl or partially cyclic $C_{7-8}$ alkyl).

Particularly preferred compounds of the invention include those wherein:

$R^1$ represents linear $C_{1-6}$ alkyl, $C_{6-10}$ cycloalkyl, or optionally substituted linear $C_{1-3}$ alkylphenyl;

R² represents OH, OC(O)R⁶ (wherein, in the latter case, R⁶ represents linear C₁₋₃ alkyl or branched C₃ alkyl), C(O)OR⁷ (wherein, in the latter case, R⁷ represents optionally substituted linear C₁₋₄ alkyl or optionally substituted branched C₃₋₄ alkyl, optionally substituted linear C₁₋₃ alkylphenyl or branched C₃ alkylphenyl) or C(O)OCH(R⁸)OC(O)R⁹ (wherein, in the latter case, R⁸ represents H and R⁹ represents C₅₋₇ cycloalkyl, linear C₁₋₆ alkyl or partially cyclic C₇₋₈ alkyl).

When R¹ represents R³ and R³ represents optionally substituted C₁₋₃ alkylphenyl, preferred optional substituent include C₁₋₆ alkyl (especially methyl).

When R² represents C(O)OR⁷ and R⁷ represents optionally substituted C₁₋₁₂ alkyl, preferred optional substituents include halogen (especially chloro) and C₁₋₆ alkoxy (especially methoxy).

When R² represents C(O)OR⁷ and R⁷ represents optionally substituted phenyl, preferred optional substituents include C₁₋₆ alkyl (especially methyl), C₁₋₆ alkoxy (especially methoxy) and halogen (especially chloro).

When R² represents C(O)OR⁷ and R⁷ represents optionally substituted C₁₋₃ alkylphenyl, preferred optional substituents include nitro.

Preferred compounds of the invention include the compounds of Examples 1 to 68.

More preferred compounds of the invention include:
EtOOCCH₂—(R)Cgl-Aze-Pab-COOCH₂CH=CH₂;
nPrOOCCH₂—(R)Cgl-Aze-Pab-COOCH₂CH=CH₂;
tBuOOCCH₂—(R)Cgl-Aze-Pab-COOCH₂CH=CH₂;
EtOOCCH₂—(R)Cgl-Aze-Pab-COOEt;
EtOOCCH₂—(R)Cgl-Aze-Pab-COO-nBu;
PrlC(O)CH₂CH₂CH₂OOCCH₂—(R)Cgl-Aze-Pab-Z;
ChNHC(O)CH₂OOCCH₂—(R)Cgl-Aze-Pab-Z;
(nPr)₂NC(O)CH₂OOCCH₂—(R)Cgl-Aze-Pab-COOCH₂OOCC(CH₃)₃;
EtOOCCH₂—(R)Cgl-Aze-Pab-COOCH₂OOCC(CH₃)₃;
EtOOCCH₂—(R)Cgl-Aze-Pab-COOCH(CH₃)OOCCH₃;
MeOOCCH₂—(R)Cgl-Aze-Pab-OOCPh;
MeOOCCH₂—(R)Cgl-Aze-Pab-OH;
EtOOCCH₂—(R)Cgl-Aze-Pab-OH;
BnOOCCH₂—(R)Cgl-Aze-Pab-OH;
nPrOOCCH₂—(R)Cgl-Aze-Pab-Z;
nPrOOCCH₂—(R)Cgl-Aze-Pab-OH;
iPrOOCCH₂—(R)Cgl-Aze-Pab-OH;
tBuOOCCH₂—(R)Cgl-Aze-Pab-OH;
(nPr)₂NCOCH₂OOCCH₂—(R)Cgl-Aze-Pab-OH;
ChNHCOCH₂OOCCH₂—(R)Cgl-Aze-Pab-OH;
EtOOCCH₂—(R)Cgl-Aze-Pab-OAc;
HOOCCH₂—(R)Cgl-Aze-Pab-OH;
HOOCCH₂—(R)Cgl-Aze-Pab-O-cis-Oleyl;
Cyclooctyl-OOCCH₂—(R)Cgl-Aze-Pab-Z;
tBuCH₂OOCCH₂—(R)Cgl-Aze-Pab-Z;
(2-Me)BnOOCCH₂—(R)Cgl-Aze-Pab-Z;
ChCH₂OOCCH₂—(R)Cgl-Aze-Pab-Z;
ChOOCCH₂—(R)Cgl-Aze-Pab-Z;
PhC(Me)₂OOCCH₂—(R)Cgl-Aze-Pab-Z;
(Me)₂CHC(Me)₂OOCCH₂—(R)Cgl-Aze-Pab-Z;
BnOOCCH₂—(R)Cgl-Aze-Pab-COOPh(4-OMe);
ChCH₂OOCCH₂—(R)Cgl-Aze-Pab-COOPh(4-OMe);
(2-Me)BnOOCCH₂—(R)Cgl-Aze-Pab-COOPh(4-OMe);
EtOOCCH₂—(R)Cgl-Aze-Pab-COOPh(4-Me);
BnOOCCH₂—(R)Cgl-Aze-Pab-COOPh(4-Me);
BnOOCCH₂—(R)Cgl-Aze-Pab-COO-nBu;
iPrOOCCH₂—(R)Cgl-Aze-Pab-COOCH₂CH=CH₂;
EtOOCCH₂—(R)Cgl-Aze-Pab-COO-iBu;
BnOOCCH₂—(R)Cgl-Aze-Pab-COO-nPr;
EtOOCCH₂—(R)Cgl-Aze-Pab-COOCH₂OOCCh;
EtOOCCH₂—(R)Cgl-Aze-Pab-COOCH₂OOCCH₂Ch;
EtOOCCH₂—(R)Cgl-Aze-Pab-COOCH(Me)OOCPh;
EtOOCCH₂—(R)Cgl-Aze-Pab-COOCH₂OOCPh;
BnOOCCH₂—(R)Cgl-Aze-Pab-COOCH(Me)OAc;
EtOOCCH₂—(R)Cgl-Aze-Pab-COOCH₂OAc;
tBuOOCCH₂—(R)Cgl-Aze-Pab-COOCH₂OAc;
MeOOC—C(=CHEt)CH₂—OOCCH₂—(R)Cgl-Aze-Pab-Z;
Men-OOCCH₂—(R)Cgl-Aze-Pab-COOPh(4-OMe); and
EtOOCCH₂—(R)Cgl-Aze-Pab-COOCH₂CCl₃.

Particularly preferred compounds of the invention include:
EtOOCCH₂—(R)Cgl-Aze-Pab-COOCH₂CCl₃;
BnOOCCH₂—(R)Cgl-Aze-Pab-COOnBu;
nPrOOCCH₂—(R)Cgl-Aze-Pab-Z;
Cyclooctyl-OOCCH₂—(R)Cgl-Aze-PabZ;
EtOOCCH₂—(R)Cgl-Aze-Pab-COOCH₂OOCCh;
MeOOCCH₂—(R)Cgl-Aze-Pab-OH;
EtOOCCH₂—(R)Cgl-Aze-Pab-OH;
nPrOOCCH₂—(R)Cgl-Aze-Pab-OH;
iPrOOCCH₂—(R)Cgl-Aze-Pab-OH;
BnOOCCH₂—(R)Cgl-Aze-Pab-OH; and
EtOOCCH₂—(R)Cgl-Aze-Pab-OAc.

Preparation

According to the invention there is also provided a process for the preparation of compounds of formula I which comprises:

(a) Preparation of a compound of formula I wherein R² represents OH by reaction of a corresponding compound of formula I, wherein R² represents OC(O)R⁶ and R⁶ is as hereinbefore defined, with an alkoxide base (eg an alkali metal alkoxide), for example at room temperature in the presence of an appropriate organic solvent (eg THF).

(b) Preparation of a compound of formula I wherein R² represents OH by reaction of a corresponding compound of formula I wherein R² represents C(O)OR⁷ and R⁷ is as hereinbefore defined with hydroxylamine, or an acid addition salt thereof, for example at room temperature in the presence of a suitable base (eg potassium carbonate or triethylamine) and an appropriate organic solvent (eg THF or EtOH).

(c) Preparation of a compound of formula I by reaction of a corresponding compound of formula II,

H—(R)Cgl-Aze-Pab-R²    II wherein R² is as hereinbefore defined with a compound of formula III,

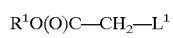

R¹O(O)C—CH₂—L¹    III wherein L¹ represents a leaving group, for example halide (eg bromide) or alkylsulphonate (eg trifluoromethylsulphonate) and R¹ is as hereinbefore defined, for example between room and elevated temperature (eg 40° C.) in the presence of a suitable base (eg potassium carbonate) and an appropriate organic solvent (eg THF, DMF or acetonitrile).

(d) Preparation of a compound of formula I wherein $R^1$ represents H and $R^2$ represents OH or $C(O)OR^7$ and $R^7$ is as hereinbefore defined by reaction of a corresponding compound of formula I wherein $R^1$ represents $C_{1-10}$ alkyl or $C_{1-3}$ alkylphenyl, and $R^2$ represents OH or $C(O)OR^7$, with a suitable base (eg an alkali metal alkoxide or hydroxide), for example at room temperature in the presence of an appropriate organic solvent (eg water or MeOH).

(e) Preparation of a compound of formula I wherein $R^2$ represents $OC(O)R^6$ and $R^6$ is as hereinbefore defined, by reaction of a corresponding compound of formula I wherein $R^2$ represents OH, with a compound of formula IV, $$R^6C(O)\text{—}O\text{—}C(O)R^6 \qquad \text{IV}$$

or a compound of formula V, $$R^6C(O)Hal \qquad \text{V}$$

wherein Hal represents Cl or Br and, in both cases, $R^6$ is as hereinbefore defined, for example at room temperature in the presence of a suitable base (eg triethylamine, pyridine or DMAP) and an appropriate organic solvent (eg methylene chloride or THF).

(f) Preparation of a compound of formula I wherein $R^1$ represents H and $R^2$ represents $OC(O)R^6$, and $R^6$ is as hereinbefore defined, by reaction of a corresponding compound of formula VI $$P^1O(O)C\text{—}CH_2\text{—}(R)Cgl\text{-}Aze\text{-}Pab\text{-}R^2 \qquad \text{VI}$$

wherein $p^1$ represents an acid labile ester protecting group (eg tBu or Bn), and $R^2$ represents $OC(O)R^6$, wherein $R^6$ is as hereinbefore defined, with a suitable acid (eg TFA), for example at room temperature in the presence of an appropriate organic solvent (eg methylene chloride).

(g) Preparation of a compound of formula I wherein $R^1$ represents $R^3$, $R^3$ represents $C_{1-10}$ alkyl or $C_{1-3}$ alkylphenyl, $R^2$ represents OH or $C(O)OR^7$, and $R^7$ is as hereinbefore defined, by a trans-esterification of a corresponding compound of formula VII, $$R^{1a}O(O)C\text{—}CH_2\text{—}(R)Cgl\text{-}Aze\text{-}Pab\text{-}R^2 \qquad \text{VII}$$

wherein $R^{1a}$ represents a $C_{1-10}$ alkyl or $C_{1-3}$ alkylphenyl group other than that being formed and $R^2$ is as hereinbefore defined or an alternative labile alkyl substituent, under conditions which are well known to those skilled in the art.

Compounds of formula II may be prepared by deprotection of a compound of formula VIII, $$\text{Boc-(R)Cgl-Aze-Pab-}R^2 \qquad \text{VIII}$$

wherein $R^2$ is as hereinbefore defined, under conditions which are well known to those skilled in the art.

Compounds of formula VI and VII may be prepared analogously to those methods described hereinbefore for preparation of compounds of formula I, in which $R^1$ represents $R^3$ and $R^3$ represents $C_{1-10}$ alkyl or $C_{1-3}$ alkylphenyl.

Compounds of formula VIII may be prepared by reaction of a compound of formula IX, $$\text{H-Pab-}R^2 \qquad \text{IX}$$

wherein $R^2$ is as hereinbefore defined with Boc-Cgl-Aze-OH, for example at room temperature in the presence of a suitable coupling system (eg EDC), an appropriate base (eg DMAP) and a suitable organic solvent (eg dichloromethane or acetonitrile).

Compounds of formula VIII, wherein $R^2$ represents OH may be prepared by reaction of a corresponding compound of formula VIII, wherein $R^2$ represents $C(O)OR^7$ or $C(O)OCH(R^8)OC(O)R^9$, with hydroxylamine, or an acid addition salt thereof, for example at room temperature in the presence of a suitable base (eg potassium carbonate or triethylamine) and an appropriate organic solvent (eg THF or EtOH).

Compounds of formula VIII, wherein $R^2$ represents $C(O)OR^7$ or $C(O)OCH(R^8)OC(O)R^9$, may be prepared by reaction of Boc-(R)Cgl-Aze-Pab-H with a compound of formula X, $$L^2C(O)OR^{2a} \qquad \text{X}$$

wherein $L^2$ represents a leaving group (eg halogen or phenolate) and $R^{2a}$ represents $R^7$ or —$CH(R_8)OC(O)R^9$ and $R^7$, $R^8$ and $R^9$ are as hereinbefore defined, for example at or below room temperature in the presence of a suitable base (eg NaOH) and an appropriate organic solvent (eg THF).

Compounds of formula VIII, wherein $R^2$ represents $OC(O)R^6$ may alternatively be prepared by reaction of a corresponding compound of formula VIII, wherein $R^2$ represents OH with a compound of formula IV as hereinbefore defined or a compound of formula V as hereinbefore defined, for example at room temperature in the presence of a suitable base (eg triethylamine, pyridine or DMAP) and an appropriate organic solvent (eg methylene chloride or THF).

Compounds of formula VIII wherein $R^2$ represents $OC(O)R^6$ may alternatively be prepared by reaction of Boc-(R)Cgl-Aze-Pab-H with a compound of formula XI, $$R^6C(O)\text{—}O\text{—}O\text{—}C(O)R^6 \qquad \text{XI}$$

wherein $R^6$ is as hereinbefore defined, for example at room temperature in the presence of an appropriate organic solvent (eg THF).

Compounds of formula VIII wherein $R^2$ represents OH may be prepared by reaction of a corresponding compound of formula VIII, wherein $R^2$ represents $OC(O)R^6$ and $R^6$ is as hereinbefore defined with a suitable base (eg an alkali metal alkoxide), for example at room temperature in the presence of an appropriate solvent (eg THF).

Compounds of formula IX are well known in the literature or may be prepared using methods analogous to those described hereinbefore. For example, compounds of formula IX wherein $R^2$ represents $C(O)OR^7$ or $C(O)OCH(R^8)OC(O)R^9$ and $R^7$, $R^8$ and $R^9$ are as hereinbefore defined may be prepared by reaction of H-Pab-H, or a protected derivative thereof, with a compound of formula X, as hereinbefore defined, for example at or below room temperature in the presence of a suitable base (eg NaOH) and an appropriate organic solvent (eg THF).

Boc-(R)Cgl-Aze-Pab-H may be prepared by reaction of H-Pab-H, or a protected derivative thereof, with Boc-Cgl-Aze-OH, for example as described hereinbefore for compounds of formula VIII.

Boc-(R)Cgl-Aze-Pab-H may alternatively be prepared by deprotection of a compound of formula XII, $$\text{Boc-(R)Cgl-Aze-Pab-}P^2 \qquad \text{XII}$$

wherein $P^2$ represents a protecting group orthogonal to Boc, under conditions which are well known to those skilled in the art.

Compounds of formula III, IV, V, X, XI and XII are either commercially available, are well known in the literature, or are available using known techniques (eg as described hereinafter).

The compounds of the invention may be isolated from their reaction mixtures using conventional techniques.

It will be appreciated by those skilled in the art that in the process described above the functional groups of intermediate compounds may need to be protected by protecting groups.

Functional groups which it is desirable to protect include hydroxy, amino, amidino and carboxylic acid. Suitable protecting groups for hydroxy include trialkylsilyl and diarylsilyl groups (eg t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino and amidino include t-butyloxycarbonyl or benzoyloxy carbonyl. Amidino nitrogens may be either mono or diprotected.

Protecting groups may be removed in accordance with techniques which are well known to those skilled in the art, such as those described hereinafter.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Medical and Pharmaceutical Use

The compounds of the invention are useful because they are metabolised in the body to form compounds which possess pharmacological activity. They are therefore indicated as pharmaceuticals and in particular as prodrugs.

In particular, the compounds of the invention, although they are inactive to thrombin per se, are metabolised in the body to form potent inhibitors of thrombin, for example as demonstrated in the test described below.

By "the compounds of the invention are inactive to thrombin per se" we mean that they exhibit an $IC_{50}TT$ value, as determined in Test A below, of greater than 1 $\mu M$.

The compounds of the invention are thus expected to be useful in those conditions where inhibition of thrombin is required.

The compounds of the invention are thus indicated both in the therapeutic and/or prophylactic treatment of thrombosis and hypercoagulability in blood and tissues of animals including man.

It is known that hypercoagulability may lead to thromboembolic diseases. Thrombo-embolic diseases which may be mentioned include activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis. The compounds of the invention are thus indicated both in the therapeutic and/or prophylactic treatment of these conditions.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis and pulmonary embolism, arterial thrombosis (eg in myocardial infarction, unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of re-occlusion (ie thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the invention may also be useful for the therapeutic and/or prophylactic treatment of idiopathic and adult respiratory distress syndrome, pulmonary fibrosis following treatment with radiation or chemotherapy, septic shock, is septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Compounds of the invention that inhibit trypsin and/or thrombin may also be useful in the treatment of pancreatitis.

According to a further aspect of the present invention, there is provided a method of treatment of a condition where inhibition of thrombin is required which method comprises administration of a therapeutically effective amount of a compound of formula I as defined above, or a pharmaceutically acceptable salt thereof, to a person suffering from, or susceptible to such a condition.

The compounds of the invention will normally be administered orally, buccally, rectally, dermally, nasally, tracheally, bronchially, by any other parenteral route or via inhalation, in the form of pharmaceutical preparations comprising the prodrug either as a free base, or a pharmaceutical acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists.

The compounds of the invention may further be combined and/or co-administered with thrombolytics such as tissue plasminogen activator (natural or recombinant), streptokinase, urokinase, prourokinase, anisolated streptokinase plasminogen activator complex (ASPAC), animal salivary gland plasminogen activators, and the like, in the treatment of thrombotic diseases, in particular myocardial infarction.

According to a further aspect of the invention there is thus provided a pharmaceutical formulation including a compound of formula I as hereinbefore defined, or a pharmaceutically acceptable salt thereof, in admixture with a pharmaceutically acceptable adjuvant, diluent or carrier.

Suitable daily doses of the compounds of the invention in therapeutical treatment of humans are about 0.001–100 mg/kg body weight at peroral administration and 0.001–50 mg/kg body weight at parenteral administration.

The compounds of the invention have the advantage that they may have improved pharmacokinetic properties, such as those identified hereinbefore, both after oral and parenteral administration, when compared with compounds of formula:

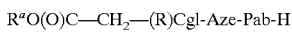
R<sup>a</sup>O(O)C—CH<sub>2</sub>—(R)Cgl-Aze-Pab-H wherein $R^a$ is as hereinbefore defined, and in particular the compound wherein $R^a$ represents H.

The compounds of the invention are inactive to thrombin, trypsin and other serine proteases. The compounds thus remain inactive in the gastrointestinal tract and the potential complications experienced by orally administered anticoagulants which are active per se, such as bleeding and indigestion resulting from inhibition of trypsin, may thus be avoided.

Furthermore, local bleeding associated with and after parenteral administration of an active thrombin inhibitor may be avoided by using the compounds of the invention.

The compounds of the invention may also have the advantage that they may be more efficacious than, be less toxic than, be longer acting than, have a broader range of activity than, produce fewer side effects than, be more easily absorbed than, or that they may have other useful pharmacological properties over, compounds known in the prior art.

Biological Tests
Test A
Determination of Thrombin Clotting Time (TT)

Human thrombin (T 6769, Sigma Chem Co, final concentration of 1.4 NIH units/mL) in buffer solution, pH 7.4, 100 μL, and inhibitor solution, 100 μL, were incubated for one min. Pooled normal citrated human plasma, 100 μL, was then added and the clotting time measured in an automatic device (KC 10, Amelung).

The clotting time in seconds was plotted against the inhibitor concentration, and the $IC_{50}TT$ was determined by interpolation.

$IC_{50}TT$ is the concentration of inhibitor that doubles the thrombin clotting time for human plasma.

Test B
Determination of Thrombin Time in Plasma ex vivo

The inhibition of thrombin after oral or parenteral administration of the compounds of the invention were examined in conscious rats which, one or two days prior to the experiment, were equipped with a catheter for blood sampling from the carotid artery. On the experimental day, the compound, dissolved in ethanol:Solutol™:water(5:5:90), was administered and blood samples were withdrawn at fixed times into plastic tubes containing 1 part sodium citrate solution (0.13 mol per L.) and 9 parts of blood. The tubes were centrifuged to obtain platelet poor plasma. The plasma was used for determination of thrombin time as described below.

The citrated rat plasma, 100 μL, was diluted with a saline solution, 0.9%, 100 μL, and plasma coagulation was started by the addition of human thrombin (T 6769, Sigma Chem Co, USA) in a buffer solution, pH 7.4, 100 μL. The clotting time was measured in an automatic device (KC 10, Amelumg, Germany).

The concentrations of the active thrombin inhibitor HO(O)C—CH<sub>2</sub>(R)Cgl-Aze-Pab-H (see International Patent Application WO 94/29336) in the rat plasma were estimated by the use of standard curves relating the thrombin time in the pooled citrated rat plasma to known concentrations of the aforementioned active thrombin inhibitor dissolved in saline.

Based on the estimated plasma concentrations of the active thrombin inhibitor HO(O)C—CH<sub>2</sub>(R)Cgl-Aze-Pab-H (which assumes that thrombin time prolongation is caused by the aforementioned compound) in the rat, the area under the curve after oral and/or parenteral administration of the prodrug was calculated (AUCpd) using the trapezoidal rule and extrapolation of data to infinity.

The bioavailability of the active thrombin inhibitor HO(O)C—CH<sub>2</sub>(R)Cgl-Aze-Pab-H after oral or parenteral administration of the prodrug was calculated as below:

[(AUCpd/dose)/(AUCactive,iv/dose)]×100 where AUCactive,iv represents the AUC obtained after intravenous administration of HO(O)C—CH<sub>2</sub>(R)Cgl-Aze-Pab-H to conscious rats as described above.

Test C
Determination of Thrombin Time in Urine ex vivo

The amount of the active thrombin inhibitor HO(O)C—CH<sub>2</sub>(R)Cgl-Aze-Pab-H that was excreted in urine after oral or parenteral administration of the compounds of the invention, dissolved in ethanol:Solutol™:water (5:5:90), was estimated by determination of the thrombin time in urine ex vivo (assuming that thrombin time prolongation is caused by the aforementioned compound).

Conscious rats were placed in metabolism cages, allowing separate collection of urine and faeces, for 24 hours following oral administration of compounds of the invention. The thrombin time was determined on the collected urine as described below.

Pooled normal citrated human plasma (100 μL) was incubated with the concentrated rat urine, or saline dilutions thereof, for one minute. Plasma coagulation was then initiated by the administration of human thrombin (T 6769, Sigma Chem Company) in buffer solution (pH 7.4; 100 μL). The clotting time was measured in an automatic device (KC 10; Amelung).

The concentrations of the active thrombin inhibitor HO(O)C—CH<sub>2</sub>(R)Cgl-Aze-Pab-H in the rat urine were estimated by the use of standard curves relating the thrombin time in the pooled normal citrated human plasma to known concentrations of the aforementioned active thrombin inhibitor dissolved in concentrated rat urine (or saline dilutions thereof). By multiplying the total rat urine production over the 24 hour period with the estimated mean concentration of the aforementioned active inhibitor in the urine, the amount of the active inhibitor excreted in the urine (AMOUNTpd) could be calculated.

The bioavailability of the active thrombin inhibitor HO(O)C—CH<sub>2</sub>(R)Cgl-Aze-Pab-H after oral or parenteral administration of the prodrug was calculated as below:

[(AMOUNTpd/dose)/(AMOUNTactive,iv/dose)]×100 where AMOUNTactive,iv represents the amount excreted in the urine after intravenous administration of HO(O)C—CH<sub>2</sub>(R)Cgl-Aze-Pab-H to conscious rats as described above.

Test D
Determination of HO(O)C—CH<sub>2</sub>—(R)Cgl-Aze-Pab-H in Urine by LC-MS The amount of the active thrombin inhibitor HO(O)C—CH<sub>2</sub>—(R)Cgl-Aze-Pab-H that was excreted in urine after oral or parenteral administration of the compounds of the invention, dissolved in ethanol:Solutol™:water (5:5:90), was measured by LC-MS analysis as described below.

The animal studies were performed as described in Method C above. Urine samples were collected and frozen at −20° C. before they were analysed.

Urine samples were analysed for their content of HO(O)C—CH<sub>2</sub>—(R)Cgl-Aze-Pab-H according to the following method:

Thawed urine samples were mixed and, if required, spinned in a centrifuge. Solid phase extraction tubes (Analytichem Bond Elut. No. 1210–2059) were activated with 1.0 mL of methanol and conditioned with 1.0 mL of acetonitrile:water (50:50), followed by 1.0 mL of 0.1% formic acid. 50 μL of the working internal standard (20 μmol/L) was added to each extraction tube. For urine standards, 50 μL of standard solution was added. 200 μL of a sample or, for urine standards, blank urine was added to each tube and thereafter pulled through via gravity or a gentle vacuum. Residual urine was washed out with 1.0 mL of ammonium acetate (2 mmol/L), before elution with 1.0 mL of acetonitrile:ammonium acetate (2 mmol/L) (35:65). The collected eluate was transferred to autosampler vials. 30 μL of the extract was injected onto the LC column (Hypersil BDS-C18; 3 μm; 75 mm×4.0 mm i.d.; Hewlett-Packard No. 79926 03-354), eluted with ammonium acetate buffer (1.3 mmol/L) with 40% acetonitrile and 0.1% formic acid at 0.75 mL/min. The effluent was split so that 30 μL/min entered the electrospray ion source of a P-E Sciex API-3 mass spectrometer. HO(O)C—$CH_2$—(R)Cgl-Aze-Pab-H and HO(O)C—$CH_2$—(R)Cgl-Pro-Pab-H (internal standard) both have retention times near 1.5 minutes. Their molecular ions ((M+H)$^+$) were monitored at m/z 430.2 and 444.2 respectively, at unit mass resolution. Urine standards at two levels, one being at the limit of quantification, were used for calibration based on peak area ratios of HO(O)C—$CH_2$—(R)Cgl-Aze-Pab-H over the internal standard. Linearity of the method was checked over the range 0.050–20 μmol/L. The coefficient of variation was 1–2% at 1–20 μmol/L and 7% at 0.50 μmol/L. The limit of quantification was 0.050 μmol/L.

By multiplying the total urine production over the 24 hour period by the measured concentration of HO(O)C—$CH_2$—(R)Cgl-Aze-Pab-H in the urine, the amount of the active inhibitor excreted in urine (AMOUNTpd) could be calculated. The bioavailability of the active thrombin inhibitor was then calculated as described in Method C above.

The invention is illustrated by way of the following examples.

EXAMPLES

General Experimental Procedures

Mass spectra were recorded on a Finnigan MAT TSQ 700 triple quadrupole mass spectrometer equipped with an electrospray interface.

The $^1$H NMR and $^{13}$C NMR measurements were performed on BRUKER ACP 300 and Varian UNITY plus 400 and 500 spectrometers, operating at $^1$H frequencies of 300.13, 399.96 and 499.82 MHz respectively, and at $^{13}$C frequencies of 75.46, 100.58 and 125.69 MHz respectively. Chemical shifts are reported in δ units.

Preparation of Starting Materials

Boc-(R)Cgl-Aze-Pab-H, Boc-(R)Cgl-Aze-Pab×HCl, H—(R)Aze-Pab-Z, H—(R)Aze-Pab-Z x HCl, Bn-OOCCH$_2$—(R)Cgl-Aze-Pab-Z, Boc-(R)Cgl-Aze-Pab-Z, Boc-(R)Cgl-Aze-OH and Pab-Z×HCl were prepared according to the methods described in International Patent Application WO 94/29336.

EXAMPLE 1

EtOOCCH$_2$—(R)Cgl-Aze-Pab-COOCH$_2$CH=CH$_2$ (i) Boc-(R)Cgl-Aze-Pab-COOCH$_2$CH=CH$_2$

To a solution of Boc-(R)Cgl-Aze-Pab-H (6.1 g; 13 mmol) in THF (125 mL) and 2M NaOH (70 mL; 140 mmol) at 0° C. was added dropwise allyl chloroformate (1.7 g; 14 mmol). After stirring at 0° C. for 1 h, the reaction was mixture concentrated, water was added (100 mL) and the resulting aqueous phase was extracted with methylene chloride (3×100 mL). The combined organic phases were concentrated to give 6.4 g of a crude product which was purified by flash chromatography using EtOAc:THF:Et$_3$N (68:29:3) as eluent. Concentration gave 5.8 g (81%) of the subtitle compound as a white solid.

$^1$H NMR (500 MHz, CDCl$_3$): δ8.19 (bt, 1H), 7.78 (d, 2H), 7.26 (d, 2H), 6.02–5.92 (m, 1H), 5.32 (d, J=17 Hz, 1H), 5.18 (d, J=10 Hz, 1H), 5.06 (d, J=7 Hz, 1H), 4.82 (bs, 1H), 4.61 (d, J=6 Hz, 2H), 4.58–4.48 (m, 1H), 4.38–4.27 (m, 2H), 4.14–4.03 (m, 1H), 3.77–3.68 (m, 1H), 2.60–0.90 (m, 24H).

$^{13}$C NMR (125 MHz, CDCl$_3$) carbonyl and amidine signals: δ172.70, 170.74, 168.02, 164.54, 155.98.

(ii) H—(R)Cgl-Aze-Pab-COOCH$_2$CH=CH$_2$×2TFA

To a solution of Boc-(R)Cgl-Aze-Pab-COOCH$_2$CH=CH$_2$ (2.03 g; 3.65 mmol; from step (i) above) in methylene chloride (15 mL) at 0° C. was added TFA (15 mL). The reaction mixture was stirred at ambient temperature for 3 h followed by concentration to give the 2.8 g of the subtitle compound as a white solid.

$^1$H NMR (500 MHz, MeOH (d4)): δ7.80 (d, 2H), 7.57 (d, 2H), 6.02 (m, 1H), 5.45 (d, J=17 Hz, 1H), 5.33 (d, J=10 Hz, 1H), 5.91–4.80 (m, 3H), 4.56 (s, 2H), 4.38 (bq, J=8 Hz, 1H), 3.71 (d, J=7 Hz, 1H), 2.76–2.60 (m, 1H), 2.35–2.20 (m, 1H), 1.9–1.0 (m, 11H).

(iii) EtOOCCH$_2$—(R)Cgl-Aze-Pab-COOCH$_2$CH=CH$_2$

A mixture of H—(R)Cgl-Aze-Pab-COOCH$_2$CH=CH$_2$×2TFA (649 mg; 0.95 mmol; from step (ii) above), K$_2$CO$_3$ (656 mg, 4.8 mmol), water (0.1 mL), and THF (10 mL) was stirred at 40° C. for 2 h followed by addition of ethyl bromoacetate (190 mg; 1.14 mmol)in THF(1 mL). After stirring at 40° C. for 4 h and at ambient temperature for 14 h the reaction mixture was filtered, concentrated, and purified by flash chromatography using EtOAc:THF:Et$_3$N (68:29:3) as eluent to give 244 mg (47%) of the title compound as a white solid.

$^1$H NMR (400 MHz, CDCl$_3$): δ8.46 (bt, 1H), 7.81 (d, 2H), 7.35 (d, 2H), 6.08–5.94 (m, 1H), 5.35 (d, J=18 Hz, 1H), 5.23 (d, J=11 Hz, 1H), 4.93 (dd, J=6 and 9 Hz, 1H), 4.66 (d, 2H), 4.62–4.38 (AB part of an ABX-spectrum), 4.16–4.04) (m, 4H), 3.20 (d, 2H), 2.86 (d, 1H), 2.64–2.45 (m, 2H), 2.0–1.0 (m 17H).

$^{13}$C NMR (100 MHz, CDCl$_3$) carbonyl and amidine signals: δ175.33, 172.24, 170.72, 168.19, 164.35.

EXAMPLE 2 nPrOOCCH$_2$—(R)Cgl-Aze-Pab-COOCH$_2$CH=CH$_2$

The title compound was prepared according to the procedure described in Example 1(iii) from H—(R)Cgl-Aze-Pab-COOCH$_2$CH=CH$_2$×2TFA (503 mg;0.74 mmol; see Example 1(ii) above) and n-propyl bromoacetate (160 mg, 0.88 mmol) to give 277 mg (68%) as a white solid.

$^1$H-NMR (400 MHz, CDCl$_3$): δ8.48 (bt, 1H), 7.83 (d, 2H), 7.35 (d, 2H), 6.76 (broad, 1H), 6.02 (m, 1H), 5.37 (dd, 1H), 5.24 (dd, 1H), 4.94 (t, 1H), 4.67 (dd, 2H), 4.49 (AB part of an ABX-spectrum, 2H), 4.12 (m, 2H), 3.98 (t, 2H), 3.24 (AB-system, 2H), 2.87 (d, 1H), 2.52 (m, 2H), 1.99 (bd, 2H), 1.80–1.50 (m, 7H), 1.61 (q, 2H), 1.30–1.10 (m, 2H), 1.00 (qd, 2H), 0.90 (t, 3H).

$^{13}$C-NMR (100 MHz, CDCl$_3$) amidine and carbonyl signals: δ175.4, 172.3, 170.7, 167.9, 164.5

EXAMPLE 3 tBuOOCCH$_2$—(R)Cgl-Aze-Pab-COOCH$_2$CH=CH$_2$

The title compound was prepared according to the procedure described in Example 1(iii) from H—(R)Cgl-Aze-Pab-COOCH$_2$CH=CH$_2$×2TFA (285 mg; 0.42 mmol; see Example 1(ii) above) and t-butyl bromoacetate (96 mg; 0.50 mmol) to give 93 mg (39%) as a white solid.

¹H NMR (500 MHz, CDCl₃): δ8.50 (bt, 1H), 7.81 (d, 2H), 7.36 (d, 2H), 6.07–5.97 (m, 1H), 5.36 (d, J=16 Hz, 1H), 5.22 (d, J=10 Hz, 1H), 4.93 (dd, J=9 and 6 Hz, 1H), 4.76 (d, J=6 Hz, 2H), 4.57–4.46 (m, 2H), 4.18–4.04 (m, 2H), 3.19–3.08 (AB-spectrum, J$_{AB}$=20 Hz, 2H), 2.86 (d, J=8 Hz, 1H), 2.72–2.53 (m, 2H), 2.0–0.9 (m, 23H).

¹³C NMR (100 MHz, CDCl₃) amidine and carbonyl signals: δ175.28, 171.53, 170.76, 167.81, 164.1.

EXAMPLE 4
EtOOCCH₂—(R)Cgl-Aze-Pab-COOEt
(i) Boc-(R)Cgl-Aze-Pab-COOEt

The sub-title compound was prepared according the procedure described in Example 1(i) from Boc-(R)Cgl-Aze-Pab-H (600 mg; 1.3 mmol) and ethyl chloroformate (150 mg; 1.4 mmol) yielding 240 mg (34%) as a white solid.

¹H-NMR (300 MHz, CDCl₃):δ 9.37 (bs, 1H), 8.16 (bs, 1H), 7.72 (d, 2H), 7.18 (d, 2H), 5.17 (d, 1H), 4.73 (t, 1H), 4.47 (dd, 1H), 4.27 (m, 2H), 4.06 (q, 2H), 3.66 (t, 1H), 2.48 (m, 1H), 2.37 (m, 1H), 1.4–1.8 (m, 7H), 1.22 (s, 9H), 1.34–0.8 (m 7H).

¹³C-NMR (75 MHz, CDCl₃) carbonyl and amidine signals: δ172.6, 170.7, 167.9, 164.8, 156.0

(ii) H—(R)Cgl-Aze-Pab-COOEt×2HCl

To a solution of Boc-(R)Cgl-Aze-Pab-COOEt (240 mg; 0.44 mmol; from step (i) above) in EtOAc (20 mL) was added hydrogen chloride at 0° C. over 5 minutes. The reaction mixture was stirred at 0° C. for 1 h followed by concentration to give 225 mg (100%) as a white solid.

¹H-NMR (300 MHz, D₂O): δ7.85 (d, 2H), 7.61 (d, 2H), 4.98 (dd, 1H), 4.60 (s, 1H), 4.44 (p, 5H), 3.90 (d, 1H), 2.73 (m, 1H), 2.37 (m, 1H), 2.0–1.65 (m, 9H), 1.39 (t, 3H), 1.4–1.1 (m, 7H), 0.98 (m, 1H). ¹³C-NMR (75 MHz, D₂O) amidine and carbonyl signals: δ172.7, 169.4, 166.8, 154.3.

(iii) EtOOCCH₂—(R)Cgl-Aze-Pab-COOEt

The title compound was prepared according to the procedure described in Example 1(iii) from H—(R)Cgl-Aze-Pab-COOEt×2HCl (160 mg; 0.31 mmol; from step (ii) above) and ethyl bromoacetate (52.5 mg; 0.31 mmol). Yield: 100 mg (61%) as a light yellow powder.

¹H-NMR (300 MHz, CDCl₃):δ 8.48 (bt, 1H), 7.81 (d, 2H), 7.38 (d, 2H), 4.51 (AB part of an ABX-spectrum, 2H), 4.21 (q, 2H), 4.15–4.05 (m, 4H), 3.21 (AB-spectrum, 2H), 2.86 (d, 1H), 2.68 (m, 1H), 2.53 (m, 1H), 1.96 (bd, 2H), 1.90–1.70 (m, 12H), 1.35 (t, 3H), 1.22 (t, 6H), 1.30–0.95 (m, 2H).

¹³C-NMR (75 MHz, CDCl₃) carbonyl and amidine signals: δ175.5, 172.2, 170.7, 167.6, 164.9

EXAMPLE 5
EtOOCCH₂—(R)Cgl-Aze-Pab-COO-nPr
(i) Boc-(R)Cgl-Aze-Pab-COO-nPr

The sub-title compound was prepared according to the procedure described in Example 1(i) above using Boc-(R) Cgl-Aze-Pab-H (6.0 g; 13 mmol;) and n-propyl chloroformate (1.57 mL; 14 mmol). Yield 5.4 g (76%).

¹H-NMR (400 MHz, CDCl₃): δ8.25 (bt, 1H), 7.82 (d, 2H), 7.31 (d, 2H), 5.09 (bd, 1H), 4.87 (dd, 1H), 4.58 (dd, 1H), 4.39 (dd, 2H), 4.14 (q, 1H), 4.10 (t, 2H), 3.79 (t, 1H), 2.54 (dm, 2H), 2.21 (s, 1H), 1.87–1.55 (m, 8H), 1.33 (s, 9H), 1.45–1.0 (m, 4H), 0.99 (t, 3H).

¹³C-NMR (100 MHz, CDCl₃) amidine and carbonyl signals: δ172.7, 170.6, 167.8, 165.0, 155.9.

(ii) H—(R)Cgl-Aze-Pab-COO-nPr×2TFA

The sub-title compound was prepared according to the procedure described in Example 1(ii) using 2.1 g (3.7 mmol) of Boc-(R)Cgl-Aze-Pab-COO-nPr (from step (i) above). Yield 3.7 g.

¹H-NMR (400 MHz, MeOH-d₄): δ7.77 (d, 2H), 7.60 (d, 1H), 4.86 (dd, 1H), 4.56 (AB part of an ABX-spectrum, 2H), 4.33 (m, 4H), 3.72 (d, 1H), 3.30 (m, 1H), 2.68 (m, 1H), 2.28 (m, 1H), 1.9–1.7 (m, 9H), 1.4–1.1 (m, 6H), 1.02 (t, 3H).

¹³C-NMR (100 MHz, MeOH-d₄) carbonyl and amidine signals: δ172.7, 169.3, 168.0, 161.4.

(iii) EtOOCCH₂—(R)Cgl-Aze-Pab-COO-nPr

The title compound was prepared according to the procedure described in Example 1(iii) from H—(R)Cgl-Aze-Pab-COO-nPr×2TFA (472 mg; 0.69 mmol; from step (ii) above) and ethyl bromoacetate (138 mg; 0.83 mmol) to give 0.22 mg (58%) as a white solid.

¹H-NMR (400 MHz, CDCl₃): δ8.46 (bt, 1H), 7.82 (d, 2H), 7.32 (d, 2H), 4.92 (dd, 1H), 4.49 (AB part of an ABX-spectrum, 2H), 4.10 (m, 6H), 3.23 (AB-spectrum, 2H), 2.80 (dm, 2H), 1.98 (bd, 2H), 1.74 (q, 2H), 1.63 (dd, 2H), 1.52 (m, 1), 1.21 (t, 3H), 1.20–1.10 (m, 2H), 0.98 (t, 3H).

¹³C-NMR (100 MHz, CDCl₃) carbonyl and amidine signals: δ175.3, 172.2, 170.7, 167.6, 164.8.

EXAMPLE 6
MeOOCCH₂—(R)Cgl-Aze-Pab-COO-nPr

The title compound was prepared according to the procedure described in Example 1(iii) above from H—(R)Cgl-Aze-Pab-COO-nPr×2TFA (365 mg; 0.53 mmol; see Example 5(ii) above) and methyl bromoacetate (98 mg; 0.64 mmol) to give 114 mg (41%) as a white solid.

¹H-NMR (500 MHz, CDCl₃): δ8.44 (bt, 1H), 7.82 (d, 2H), 7.32 ( (d, 2H), 7.04 (broad, 1H), 4.92 (dd, 1H), 4.49 (AB part of an ABX spectrum), 4.12 (m, 2H), 4.10 (t, 2H), 3.63 (s, 3H), 3.24 (s, 2H), 2.87 (d, 1H), 2.65 (m, 1H), 2.52 (m, 1H), 2.01 (broad, 1H), 1.96 (bd, 2H), 1.75 (q, 4H), 1.63 (bdd, 1H), 1.53 (m, 1H), 1.3–1.1 (m, 5H), 0.99 (t, 3H).

¹³C-NMR (100 MHz, CDCl₃) carbonyl and amidine signals: δ175.3, 172.5, 170.7, 167.7, 165.0.

EXAMPLE 7
EtOOCCH2—(R)Cgl-Aze-Pab-COOCH₂CH₂OMe
(i) Boc-(R)Cgl-Aze-Pab-COOCH₂CH₂OMe

The sub-title compound was prepared according to the procedure described in Example 1(i) above using Boc-(R) Cgl-Aze-Pab-H (6.0 g; 13 mmol) and 2-methoxyethyl chloroformate (1.94 g; 14 mmol). Yield 3.9 g (52%).

¹H-NMR (400 MHz, CDCl₃): δ8.24 (bt, 1H), 7.83 (d, 2H), 7.31 (d, 2H), 5.08 (bd, 1H), 4.87 (dd, 1H), 4.58 (dd, 1H), 4.39 (dd, 2H), 4.30 (t, 2H), 4.15 (m, 1H), 3.79 (bt, 1H), 3.68 (t, 2H), 3.40 (s, 3H), 2.65–2.45 (m, 2H), 2.20 (broad, 1H), 1.9–1.55 (m, 6H), 1.34 (s, 9H), 1.3–0.95 (m, 6H).

¹³C-NMR (100 MHz, CDCl₃) carbonyl and amidine signals: δ172.7, 170.7, 167.8, 164.6, 155.9.

(ii) H—(R)Cgl-Aze-Pab-COOCH₂CH₂OMe×2TFA

The sub-title compound was prepared according to the procedure described in Example 1(ii) above using 1.71 g of Boc-(R)Cgl-Aze-Pab-COOCH₂CH₂OMe (from step (i) above). Yield 1.89 g (88%).

¹H-NMR (400 MHz, MeOH-d4): δ7.77 (d, 2H), 7.59 (d, 2H), 4.85 (dd, 1H), 4.56 (d, 2H), 4.49 (m, 2H), 4.37 (m, 1H), 4.28 (m, 1H), 3.70 (m, 3H), 3.37 (s, 3H), 2.68 (m, 1H), 2.28 (m, 1H), 1.9–1.7 (m, 7H), 1.4–1.1 (m, 6H).

¹³C-NMR (100 MHz, MeOH-d4) carbonyl and amidine signals: δ172.7, 169.3, 168.0, 154.6.

(iii) EtOOCCH₂—(R)Cgl-Aze-Pab-COOCH₂CH₂OMe

The title compound was prepared according to the procedure described in Example 1(iii) above from H—(R)Cgl-Aze-Pab-COOCH₂CH₂OMe×2TFA (487 mg; 0.69 mmol; from step (ii) above) and ethyl bromoacetate (138 mg; 0.83 mmol) to give a crude product which was purified by flash chromatography using THF:methylene chloride (3:1) as eluent. The yield was 0.13 mg (34%) as a white solid.

¹H-NMR (400 MHz, CDCl₃): δ8.46 (bt, 1H), 7.83 (d, 2H), 7.32 (d, 2H), 7.21 (broad, 1H), 4.92 (dd, 1H), 4.49 (AB part of an ABX spectrum, 2H), 4.30 (t, 2H), 4.12 (q, 2H), 4.07 (q, 2H), 3.68 (t, 1H), 3.40 (s, 3H), 3.24 (s, 2H), 2.62 (m, 1H), 2.52 (m, 1H), 2.07 (broad, 1H), 1.97 (bd, 1H), 1.8–1.5 (m, 5H), 1.3–1.1 (m, 6H), 1.05–0.95 (m, 2H).

¹³C-NMR (100 MHz, CDCl₃) carbonyl and amidine signals: δ175.3, 172.2, 170.7, 167.8, 164.6.

EXAMPLE 8
MeOOCCH₂—(R)Cgl-Aze-Pab-COOCH₂CH₂OMe

The title compound was prepared according to the method described in Example 1(iii) above from H—(R)Cgl-Aze-Pab-COOCH₂CH₂OMe×2TFA (490 mg; 0.7 mmol; see Example 7(ii) above) and methyl bromoacetate (128 mg; 0.84 mmol) to give a crude product which was purified by flash chromatography using THF:methylene chloride (3:1) as eluent. The yield was 155 mg (41%) as a white solid.

¹H-NMR (400 MHz, CDCl₃): δ8.44 (t, 1H), 7.83 (d, 2H), 7.31 (d, 2H), 4.92 (dd, 1H), 4.49 (AB part of an ABX spectrum, 2H), 4.30 (t, 2H), 4.13 (m, 2H), 3.68 (t, 2H), 3.63 (s, 3H), 3.39 (s, 3H), 3.25 (s, 2H), 2.87 (d, 1H), 2.62 (m, 1H), 2.52 (m, 1H), 1.96 (bd, 1H), 1.8–1.5 (m, 6H), 1.3–1.1 (m, 5H), 1.00 (q, 2H).

¹³C-NMR (100 MHz, CDCl₃) carbonyl and amidine signals: δ175.2, 172.6, 170.7, 167.8, 164.5.

EXAMPLE 9
EtOOCCH₂—(R)Cgl-Aze-Pab-COO-nBu
(i) Boc-(R)Cgl-Aze-Pab-COO-nBu

The sub-title compound was prepared according to the procedure described in Example 1(i) from Boc-(R)Cgl-Aze-Pab-H (1.01 g; 2.1 mmol) and n-butyl chloroformate (0.32 g; 2.4 mmol). After stirring at ambient temperature for 1.5 h the reaction mixture was concentrated and extracted with three portions of methylene chloride. The combined organic phase was then washed with water, dried over Na₂SO₄, and concentrated to give 1.0 g (83%) of the sub-title compound as a white solid.

¹H-NMR (300 MHz, CDCl₃): δ9.81–9.31 (bs, 1H), 8.36–8.20 (m, 1H), 7.35 (d, 2H), 7.84 (d, 2H), 6.78–6.43 (bs, 1H), 5.054.82 (m, 2H), 4.69–4.15 (m, 3H), 4.15–4.08 (m, 3H), 3.86–3.70 (m, 1H), 2.68–2.42 (m, 2H), 1.92–0.88 (m, 25H).

¹³C-NMR (125 MHz, CDCl₃) amidine and carbonyl signals: δ172.5, 170.7, 167.9, 164.9, 156.0.

FAB-MS: (m+1)=572 (m/z)

(ii) H—(R)Cgl-Aze-Pab-COO-nBu×2HCl

The sub-title compound was prepared according to the procedure described in Example 4(ii) from Boc-(R)Cgl-Aze-Pab-COO-nBu (2.5 g; 4.4 mmol; from step (i) above) to give 2.4 g (100%) as a white solid.

¹H-NMR (300 MHz, MeOH-d4): δ7.78–7.60 (m, 2H), 4.66–4.49 (m, 2H), 0.98 (t, 2H), 4.49–4.35 (m, 3H), 4.35–4.22 (m, 1H), 3.75 (d, 1H), 1.92–1.67 (m, 8H), 1.56–1.07 (m, 8H). The signal of one of the protons is partially obscured by the CD₃OH-signal ¹³C-NMR (100 MHz, MeOH-d4) amidine and carbonyl signals: δ172.7, 169.3, 167.9, 154.7

MS (m+1)=472 (m/z)

(iii) EtOOCCH₂—(R)Cgl-Aze-Pab-COO-nBu

The title compound was prepared analogously to the procedure described in Example 1(iii) from H—(R)Cgl-Aze-Pab-COO-nBu×2HCl (400 mg; 0.74 mmol) and ethyl bromoacetate (147 mg; 0.88 mmol). The product was purified by flash chromatography using methylene chloride and EtOH gradient 0.1%=>12.8% as eluent to give 290 mg (70%) as a white solid.

¹H-NMR (300 MHz, CDCl₃): δ9.70–9.36 (bs, 1H), 8.47 (t, 1H), 7.81 (d, 2H), 7.32 (d, 2H), 7.07–6.73 (bs, 1H), 4.97–4.87 (dd, 1H), 4.62–4.35 (m, 2H), 4.20–3.98 (m, 6H), 3.27–3.12 (m, 2H), 2.84 (s, 1H), 2.70–2.40 (m, 2H), 2.03–0.85 (m, 22H)

¹³C-NMR (75 MHz, CDCl₃) amidine and carbonyl signals: δ175.3, 172.3, 170.8, 167.9, 165.0

FAB-MS: (m+1)=558 (m/z)

EXAMPLE 10
PrlC(O)CH₂CH₂CH₂OOCCH₂—(R)Cgl-Aze-Pab-Z
(i) PrlC(O)CH₂CH₂CH₂OH

A mixture of γ-butyrolactone (4.0 g; 46.5 mmol) and pyrrolidine (6.6 g; 92.8 mmol) was stirred at room temperature for 2.5 h. The product was concentrated in vacuum to give 14.5 g (100%) of the product as a yellow oil.

¹H-NMR (300 MHz, MeOH-d4): δ3.58 (t, 2H), 3.50 (t, 2H), 3.40 (t, 2H), 2.42 (t, 2H), 2.06–1.75 (m, 6H)

(ii) PrlC(O)CH₂CH₂CH₂OOCCH₂Br

To a mixture of PrlC(O)CH₂CH₂CH₂OH (7.2 g; 45.8 mmol; from step (i) above) and DMAP (5.6 g; 45.8 mmol) in methylene chloride at 0° C. was added dropwise bromoacetyl bromide (4.0 mL; 45.8 mmol). After stirring at room temperature for 1.5 h another portion of bromoacetyl bromide (1.0 mL, 11.4 mmol) and DMAP (1.4 g, 11.4 mmol) was added and reaction was refluxed for 1.5 h. Water was added and the methylene chloride was extracted 3 times. The organic phase was dried with Na₂SO₄ and concentrated to give 10.3 g (81%) of the product as a yellow oil.

¹H-NMR (400 MHz, CDCl₃): δ4.15 (t, 2H), 3.75 (s, 2H), 3.40–3.31 (m, 4H), 2.30 (t, 2H), 1.98–1.83 (m, 4H), 1.81–1.73 (m, 2H)

(iii) PrlC(O)CH₂CH₂CH₂OOCCH₂—(R)Cgl-Aze-Pab(Z)

The title compound was prepared according to the procedure described in Example 1(iii) from H—(R)Cgl-Aze-Pab-Z (6 g; 10.4 mmol) and PrlC(O)CH₂CH₂CH₂OOCCH₂Br (3.5 g; 12.4 mmol; from step (ii) above). The crude product was purified by flash chromatography using heptane:EtOAc:isopropanol (1:2:2) as eluent to give 4.2 g which was then purified by using preparative RPLC using 44% acetonitrile in 0.1M NH₄OAc as eluent to give 2.64 g (36%) of the product as a white solid.

¹H-NMR (500 MHz, CDCl₃): δ 9.80–9.22 (b s, 1H), 8.36 (t, 1H), 7.96–7.58 (m, 3H), 7.45 (d, 2H), 7.37–7.22 (m, 5H), 5.20 (s, 2H), 4.95–4.88 (dd, 1H), 4.72–4.29 (m, 2H), 4.15–4.04 (m, 2H), 4.04–3.88 (m, 2H), 3.40 (t, 2H), 3.34 (t, 2H), 3.28–3.17 (m, 2H), 2.85 (d, 1H), 2.67–2.48 (m, 1H), 2.23 (t, 2H), 2.14–0.93 (m, 18H).

¹³C-NMR (125 MHz, CDCl₃) amidine and carbonyl signals: δ175.3, 172.4, 170.9, 170.4, 168.2, 164.6

FAB-MS: (m+1)=703 (m/z)

EXAMPLE 11
ChNHC(O)CH₂OOCCH₂—(R)Cgl-Aze-Pab-Z
(i) ChNHC(O)CH₂OH

A mixture of cyclohexylamine (9.9 g; 99.8 mmol) and 2,5-dioxo1,4-dioxane (3.0 g, 25.9 mmol) was stirred at 100° C. for 2.5 h. The product was concentrated to give 8.1 g (100%) of the product as a brown solid.

¹H-NMR (500 MHz, MeOH-d4): δ3.92 (s, 2H), 3.75–3.65 (m, 1H), 1.90–1.58 (m, 5H), 1.43–1.07 (m, 5H). The signal of two of the protons are obscured by the CD₃OH-signal.

¹³C-NMR (125 MHz, MeOH-d4) amidine and carbonyl signals: δ174.0, 62.5, 33.7, 26.5, 26.1, 26.0 The signal of one of the carbons is obscured by the CD₃OD-signal.

(ii) ChNHC(O)CH₂OOCCH₂Br

To a mixture of ChNHC(O)CH₂OH (8.0 g; 50.9 mmol; from step (i) above) and DMAP (6.2 g; 50.9 mmol) in methylene chloride (80 mL) at 0° C. was added dropwise bromoacetyl bromide (4.0 mL; 45.8 mmol). After stirring at room temperature for 1.5 h further portions of bromoacetyl bromide (1.0 mL, 11.4 mmol) and DMAP (1.4 g, 11.4 mmol) were added and the reaction mixture was refluxed for 1.5 h. Water was added and the aqueous phase was extracted with three portions of methylene chloride. The organic phase was washed with water, dried with $Na_2SO_4$, and concentrated to give 10.3 g (73%) of the product as a brown solid.

$^1$H NMR (400 MHz, $CDCl_3$): δ6.12–6.00 (bs, 1H), 4.62 (s, 2H), 3.90 (s, 2H), 3.84–3.76 (m, 1H), 1.95–1.86 (m, 2H), 1.75–1.65 (m, 2H), 1.65–1.56 (m, 1H), 1.43–1.29 (m, 2H), 1.24–1.10 (m, 3H).

(iii) ChNHC(O)CH$_2$OOCCH$_2$—(R)Cgl-Aze-Pab-Z

The title compound was prepared analogously to the procedure described in Example 1(iii) with starting from H—(R)Cgl-Aze-Pab-Z (6 g; 10.4 mmol) and ChNHC(O)CH$_2$OOCCH$_2$Br (3.5 g; 12.4 mmol; from step (ii) above). The crude product was purified by flash chromatography using heptane:EtOAc:isopropanol (5:2:2) as eluent followed by concentration and then by preparative RPLC using 50% acetonitrile in 0.1M NH$_4$OAc as eluent. Concentration and freeze drying gave 2.6 g (36%) of the product as a white solid.

$^1$H-NMR (500 MHz, $CDCl_3$): δ9.78–9.25 (bs, 1H ), 7.90 (t, 1H), 7.78 (d, 2H), 7.44 (d, 2H), 7.38–7.24 (m, 5H), 6.66 (t, 1H), 5.20 (s, 2H), 4.90–4.83 (dd, 1H), 4.60–4.45 (m, 2H), 4.18–3.93 (m, 4H), 3.73–3.62 (m, 1H), (d, 1H), 3.23, 3.44 (AB, 2H), 2.87, 2.65–2.08 (m, 3H), 1.98–0.93 (m, 22H)

$^{13}$C-NMR (125 MHz, $CDCl_3$) amidine and carbonyl signals: δ175.1, 171.7, 170.7, 168.8, 166.1, 164.4

FAB-MS: (m+1)=703 (m/z)

EXAMPLE 12
(nPr)$_2$NC(O)CH$_2$OOCCH$_2$—(R)Cgl-Aze-Pab-COOCH$_2$OOCC(CH$_3$)$_3$ (i) (nPr)$_2$NC(O)CH$_2$OH

A mixture of 2,5-dioxo-1,4-dioxane (2.02 g; 17.4 mmol) and di-n-propylamine (5 ml; 36.5 mmol) was heated at 50° C. for 1 h and at 90° C. for 66 h. Toluene was added and subsequently removed in vacuo with excess di-n-propylamine. The residue was purified by flash chromatography using 10% methanol in methylene chloride as eluent to give 4.18 g (66%) of the desired compound.

$^1$H NMR (300 MHz, CDCl3): δ4.1 (d, 2H), 3.65 (t, 1H), 3.25–3.35 (m, 2H), 2.9–3.0 (m, 2H), 1.45–1.6 (m, 4H), 0.8–0.95 (m, 6H)

(ii) (nPr)$_2$NC(O)CH$_2$OOCCH$_2$Br

A mixture of (nPr)$_2$NC(O)CH$_2$OH (0.743 g; 4.7 mmol; from step (i) above), DCC (0.951 g, 4.6 mmol), and bromoacetic acid (0.704 g; 5.1 mmol) in methylene chloride (15 ml) was stirred at room temperature for 1.5 h. The precipitate was removed by filtration and the solvent was removed from the filtrate in vacuo. Kugelrohr distillation of the residue gave 0.66 g (50%) of the desired compound.

$^1$H NMR (300 MHz, CDCl3): δ4.8 (s, 2H), 4.0 (s, 2H), 3.2–3.3 (m, 2H), 3.05–3.15 (m, 2H), 1.5–1.7 (m, 4H), 0.8–1.0 (dt, 6H)

(iii) Pivaloyloxymethyl 4-nitrophenyl carbonate

A mixture of silver pivalate (7.5 g; 25 mmol) and iodomethyl 4-nitrophenyl carbonate (Alexander et al, J. Med. Chem. (1988) 31, 318; 7.99 g; 25 mmol) was refluxed in benzene (50 ml) for 2 h. The benzene was removed in vacuo and the residue was dissolved in toluene. Filtration through hyflo and purification by flash chromatography using toluene as eluent afforded 4.00 g (54%) of the sub-title compound.

$^1$H NMR (300 MHz; $CDCl_3$): δ8.25 (d, 2H), 7.40 (d, 2H), 5.85 (s, 2H), 1.2 (s, 2H)

$^{13}$C NMR (75 MHz, $CDCl_3$) amidine and carbonyl signals: δ176.77, 155.06

(iv) Boc-(R)Cgl-Aze-Pab-COOCH$_2$OOCC(CH$_3$)$_3$

A solution of pivalyloxymethyl 4-nitrophenyl carbonate (1.18 g; 4 mmol; from step (iii) above) in methylene chloride (20 ml) was added at room temperature to a solution of Boc-(R)Cgl-Aze-Pab-H (1.88 g; 4 mmol) and triethylamine (0.66 ml; 4.75 mmol) in methylene chloride (20 ml). After 1 h the methylene chloride was replaced by EtOAc and the mixture was purified by flash chromatography using EtOAc as eluent to give 1.27 g (50%) of sub-title compound.

$^1$H NMR (300 MHz, $CDCl_3$): δ9.5 (bs, 1H), 8.25 (t, 1H), 7.8 (d, 2H), 7.3 (d, 2H), 7.0 (bs, 1H), 5.0–4.8 (m, 2H), 4.65–4.5 (m, 1H), 4.5–4.3 (m, 2H), 4.2–4.05 (m, 1H), 3.75 (t, 1H), 2.7–2.4 (m, 2H), 1.9–1.45 (m, 5H), 1.45–0.8 (m, 24H)

(v) H—(R)Cgl-Aze-Pab-COOCH$_2$OOCC(CH$_3$)$_3$

Boc-(R)Cgl-Aze-Pab-COOCH$_2$OOCC(CH$_3$)$_3$ (327 mg; 0.52 mmol; from step (iv) above) was dissolved in a mixture of methylene chloride (5 ml) and TFA (1.2 ml). After 2 h the reaction mixture was concentrated in vacuo, acetonitrile was added, and the solvent was again removed in vacuo to give crude sub-title product which was used without further purification in the next step.

(vi) (nPr)$_2$NC(O)CH$_2$OOCCH$_2$—(R)Cgl-Aze-Pab-COOCH$_2$OOCC(CH$_3$)$_3$

The residue from step (v) above was mixed with (nPr)$_2$NC(O)CH$_2$OOCCH$_2$Br (150 mg; 0.53 mmol; from step (ii) above) and K$_2$CO$_3$ (480 mg; 3.5 mmol) in THF (5 ml) and heated for 3 h at 40° C. The reaction mixture was filtered and concentrated to a crude product which was purified by preparative RPLC to give 78 mg (21%) of the title compound.

$^1$H NMR (300 MHz, $CDCl_3$): δ9.3–9.6 (bs, 1H), 8.5 (m, 1H), 7.95–8.15 (bs, 1H), 7.85–7.95 (d, 2H), 7.2–7.3 (d, 2H), 5.8 (s, 2H), 4.8–4.9 (dd, 1H), 4.5–4.7 (m, 3H), 4.0–4.4 (m, 3H), 2.8–3.4 (m, 5H), 2.2–2.7 (m, 3H), 1.75–1.3 (m, 9H), 1.3–1.0 (m, 14H), 1.0–0.7 (m, 7H).

$^{13}$C NMR (75 MHz, CDCl3) amidine and carbonyl signals: δ177.24, 175.30, 171.85, 170.79, 168.78, 165.82, 163.14.

EXAMPLE 13
EtOOCCH$_2$—(R)Cgl-Aze-Pab-COOCH$_2$OOCC(CH$_3$)$_3$

The title compound was prepared analogously to to the procedure described in Example 12(vi) above from crude Boc-(R)Cgl-Aze-Pab-COOCH$_2$OOCC(CH$_3$)$_3$ (0.41 g; 0.65 mmol; see Example 12(iv) above) using acetonitrile (10 ml) as solvent. After stirring over night at room temperature, the solvent was removed in vacuo and the residue was partitioned between EtOAc and water. The aqueous phase was extracted three times with EtOAc and the combined organic phases were dried (Na$_2$SO$_4$) and the solvent was removed in vacuo. The residue was subjected to flash chromatography using methylene chloride/methanol as eluent. Freeze drying from glacial acetic acid gave 84 mg (21%) of the title compound.

$^1$H NMR (300 MHz, CDCl3): δ9.9 (bs, 1H), 8.5 (t, 1H), 7.35 (d, 2H), 5.85 (s, 2H), 5.90 (dd, 2H), 4.6–4.35 (m, 2H), 4.15–4.0 (m, 4), 3.2 (s, 2H), 2.85 (d, 1H), 2.7–2.45 (m, 2), 2.0–1.9 (m, 2H), 1.8–1.45 (m, 5H), 1.3–0.9 (m, 18H).

$^{13}$C NMR (75 MHz, CDCl3) amidine and carbonyl signals: δ177.23, 175.48, 172.29, 170.80, 168.85, 163.14.

EXAMPLE 14
EtOOCCH$_2$—(R)Cgl-Aze-Pab-COOCH(CH3)OOCCH$_3$ (i) Boc-(R)Cgl-Aze-Pab-COOCHC(CH$_3$)OOCCH$_3$

A solution of Boc-(R)Cgl-Aze-Pab-H (6.38 g; 13.5 mmol), 1-acetoxyethyl 4-nitrophenyl carbonate (Alexander et al, J. Med. Chem. (1988) 31, 318) (3.05 g; 12 mmol), and triethylamine (1.95 ml; 14 mmol) in methylene chloride (40 ml) was stirred at room temperature for 16 h followed by addition of EtOAc. The resulting solution was slightly concentrated and washed with aqueous $Na_2CO_3$ (10%), concentrated to a crude product, which was purified by flash chromatography using EtOAc as eluent, to give 5.59 g (77%) of the sub-title compound.

$^1$H NMR (300 MHz, CDCl3): δ9.5 (bs, 1H), 8.25 (t, 1H), 7.85 (d, 2H), 7.35 (d, 2H), 6.95 (q, 1H), 6.7 (bs, 1H), 5.0–4.85 (m, 2H), 4.65–4.5 (m, 1H), 4.5–4.25 (m, 2H), 4.2–4.05 (m, 1H)3.75 (t, 1H), 2.65–2.45 (m, 2H)2.05 (s, 3H), 1.9–1.45 (m, 11H), 1.45–0.8 (m, 12H).

$^{13}$C NMR (75 MHz, CDCl3) amidine and carbonyl signals: δ172.61, 170.80, 169.54, 168.91, 162.50, 156.02.

(ii) H—(R)Cgl-Aze-Pab-COOCH($CH_3$)OOCCH$_3$

The crude sub-title compound was prepared according to the procedure described in Example 12(v) above from Boc-(R)Cgl-Aze-Pab-COOCH(CH$_3$)OOCCH$_3$ (2.21 g; 3.68 mmol; from step (i) above).

(iii) EtOOCCH$_2$—(R)Cgl-Aze-Pab-COOCH(CH$_3$)OOCCH$_3$

The crude H—(R)Cgl-Aze-Pab-COOCH(CH$_3$)OOCCH$_3$ from step (ii) above was dissolved in methylene chloride (150 mL). The mixture was washed with a 10% $Na_2CO_3$ solution and the organic phase was dried with $K_2CO_3$ and filtered. To the resulting solution as added $K_2CO_3$ (756 mg, 5.5 mmol) and ethyl (O-trifluoromethanesulphonyl)-glycolate (790 mg; 3.3 mmol) in methylene chloride (5 ml). The reaction mixture was stirred for 5–10 minutes at room temperature and then concentrated in vacuo. The residue was dissolved in EtOAc and the resulting mixture was filtered through celite. The filtrate was subjected to flash chromatography using EtOAc as eluent followed by HPLC to give 475 mg (22%) of the title compound.

$^1$H NMR (300 MHz, CDCl3): δ9.5 (bs, 1H), 8.3 (t, 1H), 7.7 (d, 2H), 7.2 (d, 2H), 6.85 (q, 1H), 4.8 (t, 1H), 4.45–4.25 (m, 2H), 4.1–3.85 (m, 4H), 3.1 (s, 2H), 2.75 (s, 1H), 2.5–2.3 (m, 2H),1.95 (s, 3H), 1.9–1.8 (m, 1H), 1.7–1.25 (m, 8H), 1.25–1.75 (m, 8H).

$^{13}$C NMR (75.5 MHz, CDCl3) amidine and carbonyl signals: δ175.26, 172.34, 170.81, 169.49, 168.80, 162.43.

EXAMPLE 15
MeOOCCH$_2$—(R)Cgl-Aze-Pab-OOCPh (i) Boc-(R)Cgl-Aze-Pab-OOCPh

To a solution of Boc-(R)Cgl-Aze-Pab-H (1.0 g; 2.1 mmol) and Na$_2$HPO$_4$ (18.7 g; 105 mmol) in THF (45 mL) at 20° C. was added dropwise dibenzoyl peroxide (556 mg; 2.3 mmol) dissolved in THF (10 mL) over 45 minutes. After stirring at 20° C. for 24 h, the reaction mixture was concentrated and the resulting crude product was subjected to preparative RPLC. This gave 124 mg (10%) of the sub-title compound as a white solid.

$^1$H-NMR (500 MHz, CDCl$_3$): δ8.26 (m, 1H), 8.09 (m, 2H), 7.72 (m, 2H), 7.59 (m, 1H), 7.48 (m, 2H), 7.36 (d, 2H), 5.13 (s, 2H), 4.87–4.98 (m, 2H), 4.54–4.61 (m, 1H), 4.33–4.47 (m, 2H), 4.13–4.19 (m, 1H), 3.81 (t, 1H), 2.53–2.63 (m, 2H), 1.73–1.86 (m, 3H), 1.66–1.72 (m, 2H), 1.36 (s, 9H), 0.968–1.28 (m, 6H).

$^{13}$C-NMR (100 MHz, CDCl$_3$) amidine and carbonyl signals: δ6 172.7, 170.6, 163.9, 157.0, 155.9.

LC-MS: m/z 592 (M+H$^+$); m/z 614 (M+Na$^+$).

(ii) H—(R)Cgl-Aze-Pab-OOCPh

To a solution of Boc-(R)Cgl-Aze-Pab-OOCPh (600 mg; 1.01 mmol; from step (i) above) in methylene chloride (18 mL) was added TFA (6 mL) at 20° C. After stirring for 14 h, the reaction mixture was concentrated and the resulting crude product was partitioned between EtOAc:0.1 M NaOH. The phases were separated and the organic layer was dried (Na$_2$SO$_4$) and evaporated. Yield: 480 mg (96%) as a white solid.

$^1$H-NMR (400 MHz, MeOH-d4): δ8.18 (m, 2H), 7.77 (m, 2H), 7.64 (m, 1H), 7.52 (m, 2H), 7.43 (d, 2H), 4.75–4.81 (m, 1H), 4.50 (s, 2H), 4.18–4.34 (m, 2H), 3.12 (d, 1H), 2.57–2.68 (m, 1H), 2.23–2.33 (m, 1H), 1.88–1.96 (m, 1H), 1.73–1.84 (m, 2H), 1.59–1.71 (m, 2H), 1.45–1.57 (m, 1H), 0.80–1.34 (m, 5H)

LC-MS: m/z 492 (M+H$^+$); m/z 514 (M+Na$^+$)

(iii) MeOOCCH$_2$—(R)Cgl-Aze-Pab-OOCPh

To a solution of H—(R)Cgl-Aze-Pab-OOCPh (480 mg; 0.97 mmol; from step (ii) above), K$_2$CO$_3$ (270 mg; 2 mmol) in acetonitrile (5 mL) at 20° C. was added methyl bromoacetate (177 mg; 1.16 mmol). The reaction was stirred at 20° C. for 14 h. The reaction mixture was filtered and concentrated to give a crude product which was purified by preparative RPLC to give gave 269 mg (49%) of the title compound as a white solid.

$^1$H-NMR (500 MHz, CDCl$_3$): δ8.43 (m, 1H, NH), 8.09 (m, 2H), 7.69 (m, 2H), 7.59 (m, 1H), 7.47 (m, 2H), 7.34 (m, 2H), 5.27 (s, 2H), 4.93 (dd, 1H), 4.59 (dd, 1H), 4.40 (dd, 1H), 4.12 (m, 2H), 3.65 (s, 3H), 2.87 (d, 1H), 2.72–2.63 (m, 1H), 2.55–2.48 (m, 1H), 1.96 (m, 1H), 1.74 (m, 2H), 1.67 (d, 1H), 1.59 (d, 1H), 1.56–1.50 (m, 1H), 1.29–1.08 (m, 4H), 1.04–0.94 (m, 1H)

$^{13}$C-NMR (100 MHz, CDCl$_3$) amidine and carbonyl signals: δ175.1, 172.5, 170.6, 164.0, 157.1

LC-MS: m/z 564 (M+H$^+$)

EXAMPLE 16
MeOOCCH$_2$—(R)Cgl-Aze-Pab-OH

To a solution of MeOOCCH$_2$—(R)Cgl-Aze-Pab-OC(O)Ph (260 mg; 0.46 mmol; see Example 15(iii) above) in THF (4.6 mL) was added KOMe (1.6 mL; 0.29 M; 0.46 mmol) at 20° C. After 15 minutes of stirring the mixture was concentrated and subjected to preparative RPLC. This gave 109 mg (52%) of the title compound as a white solid.

$^1$H-NMR (500 MHz, MeOH-d4): δ7.59 (d, 2H), 7.34 (d, 2H), 4.83 (s, 2H), 4.82–4.76 (m, 1H), 4.48 (d, 1H), 4.33 (d, 1H), 4.15–4.30 (m,2H), 3.64 (s, 3H), 3.04 (d, 1H), 2.57 (m, 1H), 2.26 (m, 1H), 1.95 (m, 1H), 1.75 (m, 2H), 1.58–1.70 (m, 2H), 1.53 (m, 1H), 1.31–1.10 (m, 4H), 1.04 (m, 1H)

$^{13}$C-NMR (100 MHz, MeOH-d4): amidine and carbonyl signals: δ175.9, 174.3, 172.7, 155.2

LC-MS: m/z 460 (M+H$^+$), m/z 482 (M+Na$^+$)

EXAMPLE 17
EtOOCCH$_2$—(R)Cgl-Aze-Pab-OH

To a solution of EtOOCCH$_2$—(R)Cgl-Aze-Pab-C(O)OCH(CH$_3$)OOCCH$_3$ (184 mg; 0.31 mmol; see Example 14(iii) above), hydroxylamine hydrochloride (120 mg; 1.72 mmol) and triethylamine (0.8 ml; 5.7 mmol) in EtOH (95%; 4.0 mL) was added, and the mixture stirred at room temperature for 4 days. The reaction mixture was concentrated and the crude product subjected to preparative RPLC. This gave 85 mg (58%) of the title compound.

$^1$H-NMR (300 MHz, CD$_3$OD): δ7.6 (d, 2H), 7.35 (d, 2H), 4.75–4.85 m, 1H), 4.4–4.55 (m, 2H), 4.0–4.35 (m, 4H), 3.35 (d, 2H), 3.05 (d, 1H), 2.5–2.65 (m, 1H), 2.2–2.35 (m, 1H), 1.9–2.05 (m, 1H), 1.4–1.85 (m, 5H), 0.85–1.35 (m, 8H)

$^{13}$C-NMR (75.5 MHz, CD$_3$OD): amidine and carbonyl signals: δ175.97, 173.91, 172.72, 155.23

LC-MS:(m+1)=474 (m/z)

EXAMPLE 18
BnOOCCH$_2$—(R)Cgl-Aze-Pab-OH

To a solution of hydroxylamine hydrochloride (320 mg; 4.59 mmol) and triethylamine (1.7 ml; 12.24 mmol) in EtOH, BnOOCCH$_2$—(R)Cgl-Aze-Pab-Z (1.0 g; 1.52 mmol) was added. The reaction mixture was stirred at room temperature for 40 hours and then concentrated. The crude product was purified by preparative RPLC using 50% acetonitrile in 0.1M NH$_4$OAc as eluent to give 0.34 g (42%) of the title compound.

LC-MS:(m+1)=536 (m/z)

EXAMPLE 19
nPrOOCCH$_2$—(R)Cgl-Aze-Pab-Z

The title compound was prepared analogously to the procedure described in Example 1(iii) from H—(R)Cgl-Aze-Pab-Z×2HCl (700 mg; 1.2 mmol) and n-propyl bromoacetate (268 mg; 1.45 mmol). Yield 259 mg (35%).

FAB-MS:(m+1)=606 (m/z)

EXAMPLE 20
nPrOOCCH$_2$—(R)Cgl-Aze-Pab-OH

The title compound was prepared analogously to the procedure described in Example 18 from nPrOOCCH$_2$—(R)Cgl-Aze-Pab-Z (182 mg; 0.3 mmol; see Example 19 above). The crude product was purified by preparative RPLC using 40% acetonitrile in 0.1M NH$_4$OAc as eluent to give 74 mg (51%) of the desired compound.

LC-MS:(m+1)=488 (m/z)

EXAMPLE 21
iPrOOCCH$_2$—(R)Cgl-Aze-Pab-OH

The title compound was prepared analogously to the procedure described in Example 18 from iPrOOCCH$_2$—(R)Cgl-Aze-Pab-Z (590 mg; 0.7 mmol; see Example 39 below). Yield 110 mg (32%)

LC-MS:(m+1)=488 (m/z)

EXAMPLE 22
tBuOOCCH$_2$—(R)Cgl-Aze-Pab-OH

The title compound was prepared analogously to the procedure described in Example 18 from tBuOOCCH$_2$—(R)Cgl-Aze-Pab-Z (738 mg; 1.2 mmol; see Example 37 below). Yield 290 mg (48%).

LC-MS:(m +1)=502 (m/z)

EXAMPLE 23
(nPr)$_2$NCOCH$_2$OOCCH$_2$—(R)Cgl-Aze-Pab(OH)

(i) HOOCCH$_2$—(R)Cgl(Boc)-Aze-Pab-O-Boc

A solution of HOOCCH$_2$—(R)Cgl-Aze-Pab-OH (670 mg; 1.5 mmol; see Example 28 below), (Boc)$_2$O (654 mg; 3 mmol), and DMAP (92 mg; 0.75 mmol) in THF:water (10:1) was stirred at room temperature for 2 h. The reaction mixture was concentrated and purified by preparative RPLC. Freeze drying yielded 112 mg (12%) of the sub-title compound as a white solid.

LC-MS:(m−1)=643 (m/z)

(ii) (nPr)$_2$NCOCH$_2$OOCCH$_2$—(R)Cgl(Boc)-Aze-Pab-O-Boc

A solution of HOOCCH$_2$—(R)Cgl(Boc)-Aze-Pab-O-Boc (100 mg; 0.15 mmol; from step (i) above), (nPr)$_2$NCOCH$_2$OH (27 mg; 0.17 mmol; see Example 12(i) above), EDC (40 mg; 0.21 mmol) and DMAP (10 mg; 0.075 mmol) in acetonitrile (5 mL) was stirred at room temperature for 4 days. The reaction mixture was concentrated, purified by preparative RPLC and freeze dried to give 21 mg (18%) of the sub-title compound.

LC-MS:(m−1)=787 (m/z)

(iii) (nPr)$_2$NCOCH$_2$OOCCH$_2$—(R)Cgl-Aze-Pab-OH

A solution of (nPr)$_2$NCOCH$_2$—(R)Cgl(Boc)-Aze-Pab-O-Boc (20 mg; 0.025 mmol) in TFA:methylene chloride (1:1) was stirred at room temperature for 5 minutes. The reaction mixture was concentrated and freeze dried from acetonitrile and water to give 5 mg (34%) of the title compound.

LC-MS:(m+1)=587 (m/z)

EXAMPLE 24
ChNHCOCH$_2$OOCCH$_2$—(R)Cgl-Aze-Pab-OH

The title compound was prepared analogously to the procedure described in Example 18 from ChNHCOCH$_2$OOCCH$_2$ —(R)Cgl-Aze-Pab-Z (118 mg; 0.17 mmol; see Example 11(iii) above). Yield 1.8 mg.

LC-MS:(m+1)=585 (m/z)

EXAMPLE 25
MeNHCOCH$_2$OOCCH$_2$—(R)Cgl-Aze-Pab-OH

The title compound was prepared analogously to the procedure described in Example 18 from MeNHCOCH$_2$—(R)Cgl-Aze-Pab-Z (81 mg; 0.12 mmol, see Example 36 below). Yield 10 mg (16%).

LC-MS:(m+1)=517 (m/z)

EXAMPLE 26
EtOOCCH$_2$—(R)Cgl-Aze-Pab-OAc (i) H—(R)Cgl-Aze-Pab-OAc

The sub-title compound was prepared analogously to the method described in Example 27 below (steps (i), (ii) and (iii)) using acetic acid anhydride instead of propanoic acid anhydride.

LC-MS:(m+1)=430 (m/z)

(ii) EtOOCCH$_2$—(R)Cgl-Aze-Pab-OAc

The title compound was prepared analogously to the procedure described in Example 1(iii) above from H—(R)Cgl-Aze-Pab-OAc (370 mg; 0.6 mmol) and ethyl bromoacetate (105 mg; 0.63 mmol). Yield 67 mg (22%).

LC-MS:(m+1)=516 (m/z)

EXAMPLE 27
EtOOCCH$_2$—(R)Cgl-Aze-Pab-OC(O)Et (i) Boc-(R)Cgl-Aze-Pab-OH

To a solution of hydroxylamine hydrochloride and triethylamine in EtOH was added Boc-(R)Cgl-Aze-Pab-Z(1.0 g; 1.52 mmol). The reaction mixture was stirred at room temperature for 40 hours and then concentrated. The crude product was purified by preparative RPLC.

LC-MS: (m+1)=488 m/z (ii) Boc-(R)Cgl-Aze-Pab-OC(O)Et

A solution of Boc-(R)Cgl-Aze-Pab-OH (500 mg; 0.91 mmol; from step (i) above) and propanoic acid anhydride (3.5 mL) was stirred at room temperature for 45 minutes and then concentrated. The crude product was purified by preparative RPLC using 50% acetonitrile in 0.1M NH$_4$OAc as eluent to give 266 mg (54%) of the sub-title compound.

LC-MS:(m+1)=544(m/z)

(iii) H—(R)Cgl-Aze-Pab-OC(O)Et

The sub-title compound was prepared analogously to the procedure described in Example 1(ii) from Boc-(R)Cgl-Aze-Pab-OC(O)Et (238 mg; 0.44 mmol; from step (ii) above). Yield 290 mg (100%).

LC-MS:(m+1)=444(m/z)

(iv) EtOOCCH$_2$—(R)Cgl-Aze-Pab-OC(O)Et

To a solution of H—(R)Cgl-Aze-Pab-OOCEt(300 mg; 0.45 mmol; from step (iii) above) and K$_2$CO$_3$ (308 mg; 2.23 mmol) in methylene chloride (6 mL) at 0° C. was added dropwise EtOOCCH$_2$OSO$_2$CF$_3$ (105 mg; 0.45 mmol, prepared from triflic anhydride and ethyl glycolate). After the reaction mixture was stirred at room temperature for 1 h the reaction mixture was washed with water, citric acid and water, dried (Na$_2$SO$_4$) and concentrated. The crude product was purified by preparative RPLC using 45% acetonitrile in 0.1M NH$_4$OAc as eluent to give 63 mg (27%) of the title compound.

LC-MS:(m+1)=530(m/z)

EXAMPLE 28

HOOCCH$_2$—(R)Cgl-Aze-Pab-OH (i) tBuOOCCH$_2$—(R)Cgl-Aze-Pab-OOCPh

The sub-title compound was prepared analogously to the procedure described in Example 1(iii) from H—(R)Cgl-Aze-Pab-OOCPh (250 mg; 0.5 mmol; see Example 15(ii) above) and t-butylbromoacetate (119 mg; 0.6 mmol). Yield 211 mg (69%).

LC-MS:(m+1)=606 (m/z)

(ii) HOOCCH$_2$—(R)Cgl-Aze-Pab-OOCPh

The sub-title compound was prepared analogously to the procedure described in Example 1(ii) from tBuOOCCH$_2$—(R)Cgl-Aze-Pab-OOCPh (233 mg; 0.3 mmol; from step (i) above). Yield 65 mg (37%).

LC-MS:(m+1)=550 (m/z)

(iii) HOOCCH$_2$—(R)Cgl-Aze-Pab-OH

A solution of HOOCCH$_2$—(R)Cgl-Aze-Pab-OOCPh (60 mg; 0.1 mmol; from step (ii) above) and KOMe (0.2M; 0.2 mmol) in THF (10 mL) and methanol (1.5 mL) was stirred at room temperature for 5 minutes. The reaction mixture was concentrated and freeze dried from water and acetonitrile to give 28 mg (63%) of the title compound.

LC-MS:(m+1)=446(m/z)

EXAMPLE 29

HOOCCH$_2$—(R)Cgl-Aze-Pab-O-cis-Oleyl (i) tBuOOCCH2—(R)Cgl(Boc)-Aze-Pab-Z

A solution of tBuOOCCH$_2$—(R)Cgl-Aze-Pab-Z (1.7 g, 2.8 mmol; see Example 37 below), (Boc)$_2$O (672 mg; 3.08 mmol) and DMAP (68 mg; 0.56 mmol) in THF (30 mL) was stirred at room temperature for 24 h. Additional (Boc)$_2$O (305 mg; 1.4 mmol) was added at 5° C. After another 24 h the reaction mixture was concentrated and purified by preparative RPLC to give 587 mg (30%) of the desired compound.

EC-MS:(m+1)=720 (m/z)

(ii) tBuOOCCH$_2$—(R)Cgl(Boc)-Aze-Pab-OH

The sub-title compound was prepared analogously to the procedure described in Example 18 from tBuOOCCH$_2$—(R)Cgl(Boc)-Aze-Pab-Z (580 mg; 0.8 mmol; from step (i) above). Yield 341 mg (71%).

EC-MS:(m+1)=602 (m/z)

(iii) tBuOOCCH$_2$—(R)Cgl(Boc)-Aze-Pab-O-cis-Oleyl

A solution of tBuOOCCH$_2$—(R)Cgl(Boc)-Aze-Pab-OH (340 mg; 0.56 mmol; from step (ii) above), cis-oleylchloride (170 mg; 0.56 mmol) and triethylamine (62 mg; 0.61 mmol) in methylene chloride was stirred for 5 minutes. The reaction mixture was concentrated and purified by preparative RPLC to give 326 mg (67%) of the sub-title compound.

EC-MS:(m+1)=867(m/z)

(iv) HOOCCH$_2$—(R)Cgl-Aze-Pab-O-cis-Oleyl

The title compound was prepared analogously to the procedure described in Example 1(ii) from tBuOOCCH$_2$—(R)Cgl(Boc)-Aze-Pab-O-cis-Oleyl (223 mg; 0.25 mmol; from step (iii) above).

LC-MS:(m+1)=710 (m/z)

EXAMPLE 30

Cyclooctyl-OOCCH$_2$—(R)Cgl-Aze-Pab-Z (i) Cyclooctyl-bromoacetate

Cyclooctanol (1.3 g; 10 mmol) and DMAP (0.3 g) was dissolved in methylene chloride followed by addition of bromacetyl chloride (1 mL; 12 mmol). After stirring for 18 h the reaction mixture was washed with aqueous Na$_2$CO$_3$ (2M) and HCl (1M), dried, concentrated and purified by flash chromatography using petroleum ether:methylene chloride (50:50) to give 1.8 g (72%) of the sub-title compound.

(ii) Cyclooctyl-OOCCH$_2$—(R)Cgl-Aze-Pab-Z

The title compound was prepared analogously to the procedure described in Example 1(iii) from H—(R)Cgl-Aze-Pab-Z×2HCl (703 mg; 1.2 mmol) and cyclooctyl bromoacetate (363 mg; 1.46 mmol; from step (i) above). Yield 379 mg (46%).

FAB-MS:(m+1)=674(m/z)

EXAMPLE 31 tBuCH$_2$OOCCH$_2$—(R)Cgl-Aze-Pab-Z

The title compound was prepared analogously to the procedure described in Example 1(iii) from H—(R)Cgl-Aze-Pab-Z×2HCl (2.5 g; 4.3 mmol) and tertbutylmetyl bromoacetate (1.08 g; 5.2 mmol). Yield 1.87 g (69%).

FAB-MS:(m+1)=634 (m/z)

EXAMPLE 32

(2-Me)BnOOCCH$_2$—(R)Cgl-Aze-Pab-Z (i) Methylbenzyl bromoacetate

The sub-title compound was prepared analogously to the procedure described in Example 30(i) from 2-methylbenzylalcohol (5 g; 41 mmol) and bromacetyl chloride (12.6 g; 80 mmol). Yield 8.2 g (82%).

(ii) (2Me)BnOOCCH$_2$—(R)Cgl-Aze-Pab-Z

The title compound was prepared analogously to the procedure described in Example 1(iii) from H—(R)Cgl-Aze-Pab-Z×2HCl (580 mg; 1 mmol) and 2-methylbenzyl bromoacetate (290 mg; 1.2 mmol; from step (i) above). Yield 30 mg (4.5%).

LC-MS:(m+1)=668 (m/z)

EXAMPLE 33

ChCH$_2$OOCCH$_2$—(R)Cgl-Aze-Pab-Z

A solution of BnOOCCH$_2$—(R)Cgl-Aze-Pab-Z (1.41 g; 1.7 mmol) and cyclohexyl methylalcohol (6 mL) in triethylamine (474 µL) and methylene chloride (3 mL) was refluxed for 4 days. The reaction mixture was worked up to give a crude product which was purified by flash chromatography using methylene chloride:methanol (95:5) as eluent to give 801 mg (71%) of the title compound.

FAB-MS:(m+1)=660 (m/z)

EXAMPLE 34

ChOOCCH$_2$—(R)Cgl-Aze-Pab-Z (i) Cyclohexyl bromoacetate

The sub-title compound was prepared analogously to the procedure described in Example 32(i) above from cyclohexanol (1 g; 10 mmol) and bromacetylchloride (1 mL; 12 mmol).

(ii) ChOOCCH$_2$—(R)Cgl-Aze-Pab-Z

The title compound was prepared analogously to the procedure described in Example 1(iii) from H—(R)Cgl-Aze-Pab-Z×2HCl(2.5 g; 4.32 mmol) and cyclohexyl bromoacetate (1.5 g; 5.2 mmol). Yield 1.7 g (60%).

FAB-MS:(m+1)=646 (m/z)

EXAMPLE 35

PhC(Me)$_2$OOCCH$_2$—(R)Cgl-Aze-Pab-Z (i) 2-Phenyl-2-propyl bromoacetate

The sub-title compound was prepared analogously to the procedure described in Example 30(i) from 2-phenyl-2-propanol (3 g; 22 mmol) and bromacetylchloride (4.16 g, 26 mmol). Yield 1.2 g (44%).

(ii) PhC(Me)$_2$OOCCH$_2$—(R)Cgl-Aze-Pab-Z

The title compound was prepared analogously to the procedure described in Example 1(iii) from H—(R)Cgl-Aze-Pab-Z×2HCl (1.2 g; 2.2 mmol) and 2-phenyl-2-propyl bromoacetate (640 mg; 2.5 mmol; from step (i) above). Yield 1.3 g (86%).

$^1$H-NMR (500 MHz; CDCl$_3$) δ9.3 (br s, 1H), 8.35 (t, 1H), 7.75 (d, 2H), 7.45 (d, 2H), 7.30–7.05 (m, 10H or 11H), 5.15 (s, 2H), 4.78 (t, 1H), 4.40–4.30(AB part of ABX spectrum, 2H), 3.95 (q, 1H), 3.74 (q, 1H), 3.27–3.19 (AB-spectrum, 2H), 2.72 (d, 1H), 2.43 (q, 2H), 1.93 (br d, 1H), 1.75–1.60 (m, 9H or 10H), 1.54 (d, 1H), 1.49–1.40 (m, 1H), 1.25–1.0 (m, 4H), 0.92 (q, 1H)

EXAMPLE 36
MeNHCOCH$_2$OOCCH$_2$—(R)Cgl-Aze-Pab-Z

The title compound was prepared analogously to the procedure described in Example 1(iii) from H—(R)Cgl-Aze-Pab-Z×2HCl (1.0 g; 1.7 mmol) and MeNHCOCH$_2$OOCCH$_2$Br (440 mg; 2 mmol; prepared analogously to the procedures described in Example 11 above (steps (i), (ii) and (iii)) using methylamine instead of cyclohexylamine). Yield 380 mg (35%).

FAB-MS:(m+1)=635 (m/z)

EXAMPLE 37
tBuOOCCH$_2$—(R)Cgl-Aze-Pab-Z

The title compound was prepared analogously to the procedure described in Example 1(iii) from H—(R)Cgl-Aze-Pab-Z×2HCl (500 mg; 1.0 mmol) and t-butyl bromoacetate (231 mg; 1.2 mmol). Yield 420 mg (69%).

LC-MS:(m +1)=620 (m/z)

EXAMPLE 38
(Me)$_2$CHC(Me)$_2$OOCCH$_2$—(R)Cgl-Aze-Pa

The title compound was prepared analogously to the procedure described in Example 1(iii) from H—(R)Cgl-Aze-Pab-Z (787 mg; 1.4 mmol) and 2,3-dimethyl-2-butyl bromoacetate (364 mg; 1.63 mmol). Yield 590 mg (67%).

FAB-MS:(m+1)=648(m/z)

EXAMPLE 39
iPrOOCCH$_2$—(R)Cgl-Aze-Pab-Z

The title compound was prepared analogously to the procedure described in Example 1(iii) from H—(R)Cgl-Aze-Pab-Z (700 mg; 1.2 mmol) and isopropyl bromoacetate (262 mg; 1.5 mmol). Yield 225 mg (31%)

FAB-MS:(m+1)=606(m/z)

EXAMPLE 40
BnOOCCH$_2$—(R)Cgl-Aze-Pab-COOPh(4-OMe)

(i) Boc-(R)Cgl-Aze-Pab-COOPh(4-OMe)

The sub-title compound was prepared analogously to the procedure described in Example 1(i) from Boc-(R)Cgl-Aze-Pab-H and 4-methoxyphenyl chloroformate.

FAB-MS:(m+1)=622(m/z)

(ii) H—(R)Cgl-Aze-Pab-COOPh(4-OMe)×2HCl

The sub-title compound was prepared analogously to the procedure described in Example 4(ii) from Boc-(R)Cgl-Aze-Pab-COOPh(40OMe) (from step (i) above).

(iii) BnOOCCH$_2$—(R)Cgl-Aze-Pab-COOPh(4-OMe)

The title compound was prepared analogously to the procedure described in Example 1(iii) from H—(R)Cgl-Aze-Pab-COOPh(4-OMe)×2HCl(85 mg; 0.16 mmol; from step (iii) above) and benzyl bromoacetate (90 mg; 0.2 mmol). Yield 60 mg (56%).

FAB-MS:(m+1)=670 (m/z)

EXAMPLE 41
ChCH$_2$OOCCH$_2$—(R)Cgl-Aze-Pab-COOPh(4-OMe)

The title compound was prepared analogously to the procedure described in Example 1(iii) from H—(R)Cgl-Aze-Pab-COOPh(4-OMe) (554 mg; 0.64 mmol; see Example 40(ii) above) and cyclohexylmethyl bromoacetate (165 mg; 0.7 mmol). Yield 34 mg (8%).

FAB-MS:(m+1)=676 (m/z)

EXAMPLE 42
(2-Me)BnOOCCH$_2$—(R)Cgl-Aze-Pab-COOPh(4-OMe)

The title compound was prepared analogously to the procedure described in Example 1(iii) from H—(R)Cgl-Aze-Pab-COOPh(4-OMe) (522 mg; 1 mmol; see Example 40(ii) above) and 2-(methyl)benzyl bromoacetate (365 mg; 1.5 mmol). Yield 158 mg (23%).

LC-MS:(m+1)=684 (m/z)

EXAMPLE 43
EtOOCCH$_2$—(R)Cgl-Aze-Pab-COOPh(4-Me)

(i) Boc-(R)Cgl-Aze-Pab-COOPh(4-Me)

The sub-title compound was prepared analogously to the procedure described in Example 1(i) from Boc-(R)Cgl-Aze-Pab (1.96 g; 4.56 mmol) and 4tolyl-chloroformate (850 mg; 4.99 mmol). Yield 1.39 g (55%).

FAB-MS:(m+1)=606(m/z)

(ii) H—(R)Cgl-Aze-Pab-COOPh(4-Me)

The sub-title compound was prepared analogously to the procedure described in Example 4(ii) from Boc-(R)Cgl-Aze-Pab-COOPh(4Me) (388 mg; 0.64 mmol; from step (i) above). Yield 293 mg (91%).

FAB-MS:(m+1)=506(m/z)

(iii) EtOOQCCH$_2$—(R)Cgl-Aze-Pab-COOPh(4-Me)

The title compound was prepared analogously to the procedure described in Example 1(iii) from H—(R)Cgl-Aze-Pab-COOPh(4-Me) (288 mg; 0.6 mmol; from step (ii) above) and ethyl bromoacetate (114 mg; 0.7 mmol). Yield 81 mg (24%).

FAB-MS:(m+1)=592 (m/z)

EXAMPLE 44
BnOOCCH$_2$—(R)Cgl-Aze-Pab-COOPh(4-Me)

The title compound was prepared analogously to the procedure described in Example 1(iii) from H—(R)Cgl-Aze-Pab-COOPh(4-Me) (272 mg; 0.54 mmol; see Example 43(ii) above) and benzyl bromoacetate (147 mg; 0.6 mmol). Yield 107 mg (31%).

FAB-MS:(m+1)=654(m/z)

EXAMPLE 45
BnOOCCH$_2$—(R)Cgl-Aze-Pab-COO-nBu

The title compound was prepared analogously to the procedure described in Example 1(iii) from H—(R)Cgl-Aze-Pab-COO-nBu×2HCl (400 mg; 0.74 mmol; see Example 9(ii) above) and benzyl bromoacetate (210 mg; 0.88 mmol). Yield 220 mg (48%).

FAB-MS:(m+1)=620 (m/z)

EXAMPLE 46
iPrOOCCH$_2$—(R)Cgl-Aze-Pab-COOCH$_2$CH=CH$_2$

The title compound was prepared analogously to the procedure described in Example 1 (iii) from H—(R)Cgl-Aze-Pab-COOCH$_2$CH=CH$_2$×2TFA (456 mg; 0.67 mmol; see Example 1(ii) above) and isopropyl bromoacetate (145 mg; 0.8 mmol). Yield 294 mg (79%).

FAB-MS:(m+1)=556 (m/z)

EXAMPLE 47

EtOOCCH$_2$—(R)Cgl-Aze-Pab-COO-iBu (i) Boc-Pab-COO-iBu

To a solution of Boc-Pab-H (500 mg; 2.0 mmol; prepared from Pab-Z and (Boc)$_2$O (forming Boc-Pab-Z), followed by hydrogenation over Pd/C) and triethylamine (400 mg; 4.0 mmol) in methylene chloride (10 mL) was added i-butyl chloroformate (270 mg; 2.2 mmol) at 0° C. After stirring for 5 h, water was added. The organic phase was dried (Na$_2$SO$_4$) and concentrated to give 530 mg (76%) of the sub-title compound.

$^1$H-NMR (500 MHz, CDCl$_3$) δ9.5 (bs, 1H), 7.82 (d, 2H), 7.31 (d, 2H), 6.6 (bs, 1H), 5.0 (bs, 1H), 4.33 (bd, 2H), 3.93 (d, 2H), 2.04 (m, 1H), 1.45 (s, 9H), 0.97 (d, 6H)

(ii) H—Pab-COO-iBu×2HCl

The sub-title compound was prepared analogously to the procedure described in Example 4(ii) from Boc-Pab-COO-iBu (520 mg; 1.5 mmol; from step (i) above). Yield 430 mg (88%).

$^1$H-NMR (500 MHz, MeOD) δ7.89 (d, 2H), 7.75 (d, 2H), 4.30 (s, 2H), 4.17 (d, 2H), 2.11–2.05 (m, 1H), 1.02 (d, 6H)

(iii) Boc-(R)Cgl-Aze-Pab-COO-iBu

To a solution of Boc-(R)Cgl-Aze-OH (480 mg; 1.4 mmol), H—Pab-COO-iBu ×2HCl (430 mg; 1.3 mmol; from step (ii) above) and DMAP (650 mg; 5.3 mmol) in acetonitrile (20 mL) was added EDC (270 mg; 1.4 mmol). After stirring for 3 days at room temperature the reaction mixture was concentrated and then dissolved in water and EtOAc. The organic phase was washed with NaHCO$_3$ (aq) and dried (Na$_2$SO$_4$), concentrated and purified by flash chromatography using EtOAc as eluent to give 510 mg (52%) of the sub-title compound.

(iv) H—(R)Cgl-Aze-Pab-COO-iBu×2HCl

The sub-title compound was prepared analogously to the procedure described in Example 4(ii) from Boc-(R)Cgl-Aze-Pab-COO-iBu (500 mg; 0.88 mmol; from step (iii) above). Yield 360 mg (87%).

(v) EtOOCCH$_2$—(R)Cgl-Aze-Pab-COO-iBu

The title compound was prepared analogously to the procedure described in Example 1(iii) from H—(R)Cgl-Aze-Pab-COO-iBu×2HCl (290 mg; 0.53 mmol; from step (iv) above) and ethyl bromoacetate (110 mg; 0.64 mmol). Yield 140 mg (47%).

FAB-MS:(m+1)=558 (m/z)

EXAMPLE 48

BnOOCCH$_2$—(R)Cgl-Aze-Pab-COO-nPr

The title compound was prepared analogously to the procedure described in Example 1(iii) from H—(R)Cgl-Aze-Pab-COO-nPr×2TFA (902 mg; 1.3 mmol; see Example 5(ii) above) and benzyl bromoacetate (362 mg; 1.6 mmol). Yield 199 mg (25%).

$^1$H-NMR: (400 MHz; CDCl$_3$) δ8.43 (bs, 1H), 7.78 (d, 2H), 7.38–7.27 (m, 7H), 5.05 (s, 2H), 4.90 (dd, 1H), 4.56–4.39 (AB part of ABX spectrum, 2H), 4.12–4.03 (m, 3H), 3.98–3.91 (q, 1H), 3.33–3.22 (AB-spectrum, 2H), 2.85 (d, 1H), 2.65–0.94 (m, 19H)

EXAMPLE 49

EtOOCCH$_2$—(R)Cgl-Aze-Pab-COOCH$_2$OOCCh (i) EtSCOOCH$_2$OOCCh

To a solution of tetrabutylammonium hydrogensulphate (15.6 g, 45.6 mmol) and cyclohexane carboxylic acid (5.85 g, 46 mmol) in methylene chloride was added NaOH (9.1 mL,10M; 68 mmol) at 0° C. After stirring for 5 minutes the reaction mixture was filtered, washed with methylene chloride, dissolved in toluene, concentrated and dissolved in THF to give [Bu$_4$N]$^+$[OOCCh]$^-$. EtSCOOCH$_2$Cl (4 g; 25.9 mmol; see Folkmann and Lund, J. Synthesis, (1990), 1159) was added to the THF solution of [Bu$_4$N]$^+$[OOCCh]$^-$ at room temperature. After stirring at room temperature for 12 h the reaction mixture was concentrated and purified by flash chromatography to give 2.57 g (40%) of the sub-title compound.

$^1$H-NMR (400 MHz, CDCl$_3$) diagnostic peaks δ5.80 (s, 2H, O—CH$_2$—O), 2.85 (q, 2H, CH$_2$—S)

(ii) ClCOOCH$_2$OOCCh

To EtSCOOCH$_2$OOCCh (2.9 g; 11.8 mmol; from step (i) above) was added dropwise SO$_2$Cl$_2$ (3.18 g; 23.6 mmol) at 0° C. After stirring for 30 minutes the reaction mixture was concentrated to give 1.82 g (70%) of the desired compound.

$^1$H-NMR (500 MHz, CDCl$_3$) diagnostic peaks δ5.82 (s, 2H, O—CH$_2$—O)

(iii) Boc-(R)Cgl-Aze-Pab-COOCH$_2$OOCCh

The sub-title compound was prepared analogously to the procedure described in Example 1(i) from Boc-(R)Cgl-Aze-Pab-H (750 mg; 20 1.59 mmol) and ClCOOCH$_2$OOCCh (460 mg; 2.1 mmol; from step (ii) above). The crude product was purified by preparative RPLC. Yield 355 mg (9%).

FAB-MS:(m+1)=656(m/z)

(iv) H—(R)Cgl-Aze-Pab-COOCH$_2$OOCCh×2TFA

The sub-title compound was prepared analogously to the procedure described in Example 1(ii) from Boc-(R)Cgl-Aze-Pab-COOCH$_2$OOCCh (from step (iii) above).

(v) EtOOCCH$_2$—(R)Cgl-Aze-Pab-COOCH$_2$OOCCh

The title compound was prepared analogously to the procedure described in Example 1(iii) from H—(R)Cgl-Aze-Pab-COOCH$_2$OOCCh×2TFA (193 mg; 0.35 mmol; from step (iv) above) and ethyl trifluoroacetate (83 mg; 0.35 mmol). Yield 87 mg (39%).

$^1$H-NMR (400 MHz, CDCl$_3$) δ8.48 (t br, 1H), 7.83 (d, 2H), 7.37 (d, 2H), 5.86 (s, 2H), 4.95 (dd, 1H), 4.15–4.39 (AB part of ABX spectrum, 2H), 4.18–4.05 (m, 5H), 3.26–3.17 (AB-spectrum, 2H), 2.87 (d, 1H), 2.75–0.95 (m, 29H)

EXAMPLE 50

EtOOCCH$_2$—(R)Cgl-Aze-Pab-COOCH$_2$OOCCH$_2$Ch

The title compound was prepared analogously to the procedure described in Example 49 above starting with cyclohexyl acetic acid instead of cyclohexane carboxylic acid. Yield 74 mg (17%).

FAB-MS:(m+1)=656(m/z)

EXAMPLE 51

EtOOCCH$_2$—(R)Cgl-Aze-Pab-COOCH(Me)OOCPh

The title compound was prepared analogously to the procedure described in Example 49 above starting with EtSCOOCH(CH$_3$)Cl (prepared from ClCOCH(CH$_3$)Cl and EtSH using the procedure described by Folkmann et al in J. Synthesis, (1990), 1159) instead of EtSCOOCH$_2$Cl. Yield 70 mg (23%).

FAB-MS:(m+1)=650 (m/z)

EXAMPLE 52

EtOOCCH$_2$—(R)Cgl-Aze-Pab-COOCH$_2$OOCPh

The title compound was prepared analogously to the procedure described in Example 49 above using benzoic acid instead of cyclohexane carboxylic acid. Yield 50 mg (39%).

$^1$H-NMR (300 MHz, CDCl$_3$) δ9.73–9.25 (s br, 1H), 8.45 (t, 1H), 8.05 (d, 2H), 7.83 (d, 2H), 7.60–7.10 (m, 6H), 6.10 (s, 2H), 4.96–4.84 (dd, 1H), 4.62–4.30 (ABX, 2H), 4.20–3.93 (m, 4H), 3.25 (s, 2H), 2.84 (d, 1H), 2.73–2.41 (m, 2H), 2.41–0.87 (m, 15H)

$^{13}$C-NMR (300 MHz, CDCl$_3$, amidine and carbonyl carbons) δ163.1, 165.3, 169.0, 170.8, 172.3, 175.5

EXAMPLE 53
BnOOCCH$_2$—(R)Cgl-Aze-Pab-COOCH(Me)OAc

The title compound was prepared analogously to the procedure described in Example 1(iii) from H—(R)Cgl-Aze-Pab-COOCH(CH$_3$)OC(O)CH$_3$ (108 mg; 0.21 mmol; see Example 14(ii) above) and benzyl bromoacetate (36μL; 0.23 mmol). Yield 41 mg (30%).

FAB-MS: (m+1)=650(m/z)

EXAMPLE 54
EtOOCCH$_2$—(R)Cgl-Aze-Pab-COOCH$_2$OAc (i) H—(R)Cgl-Aze-Pab-COOCH$_2$OAc×2TFA

The sub-title compound was prepared analogously to the procedure described in Example 14 (steps (i) and (ii)) above using acetoxymethyl 4-nitrophenylcarbonate (prepared analogously to the method described in Example 12(iii) using silver acetate instead of silver pivalate). Work up gave the sub-title compound which was used in the next step without further purification.

(ii) EtOOCCH$_2$—(R)Cgl-Aze-Pab-COOCH$_2$OAc

The title compound was prepared analogously to the procedure described in Example 1(iii) above from H—(R)Cgl-Aze-Pab-COOCH$_2$OAc×2TFA (0.83 mmol; from step (i) above) and ethyl bromoacetate (2.2 mmol). Yield 286 mg.

FAB-MS:(m+1)=574 (m/z)

EXAMPLE 55
tBuOOCCH$_2$—(R)Cgl-Aze-Pab-COOCH$_2$OAc

The title compound was prepared analogously to the procedure described in Example 1(iii) above from H—(R)Cgl-Aze-Pab-COOCH$_2$OAc×2TFA (0.313 mmol; see Example 54(i) above) and t-butyl bromoacetate (73 mg; 0.376 mmol). Yield 156 mg (83%).

FAB-MS:(m+1)=602(m/z)

EXAMPLE 56
BnOOCCH$_2$—(R)Cgl-Aze-Pab-COOCH$_2$OOC-tBu

The title compound was prepared analogously to the procedure described in Example 1(iii) from H—(R)Cgl-Aze-Pab-COOCH2OOC-tBu (379 mg; 0.71 mmol; see Example 12(v) above) and benzyl bromoacetate (135 μL; 0.85 mmol). Yield 146 mg (30%).

FAB-MS:(m+1)=678(m/z)

EXAMPLE 57
EtOOCCH$_2$—(R)Cgl-Aze-Pab-COOCH$_2$CCl$_3$ (i) Boc-(R)Cgl-Aze-Pab-COOCH$_2$CCl$_3$

The sub-title compound was prepared analogously to the procedure described in Example 1(i) from Boc-(R)Cgl-Aze-Pab-H (1.0 g; 2.12 mmol), 2M NaOH (11.7 ml) and trichloroethyl chloroformate (494 mg; 2.33 mmol). Yield 1.08 g (79%).

(ii) H—(R)Cgl-Aze-Pab-COOCH$_2$CCl$_3$

The sub-title compound was prepared analougously to the procedure described in Example 1(ii) from Boc-(R)Cgl-Aze-Pab-COOCH$_2$CCl$_3$ (1.04 g; 1.607 mmol; from step (i) above). Yield 1.43 g (99%).

$^1$H-NMR: (500 MHz; CD$_3$OD) δ7.79 (d, 2H), 7.61 (d, 2H), 5.10 (s, 2H), 4.87–4.81 (m, 2H), 4.63–4.52 (q, 2H), 4.41–4.34 (m, 1H), 4.30–4.24 (m, 1H), 3.72 (d, 1H), 2.72–2.63 (m, 1H), 2.32–2.25 (m, 1H), 1.88–1.10 (m, 14H)

(iii) EtOOCCH$_2$—(R)Cgl-Aze Pab-COOCH$_2$CCl$_3$

The title compound was prepared analogously to the procedure described in Example 1(iii) from H—(R)Cgl-Aze-Pab-COOCH$_2$CCl$_3$ (400 mg; 0.52 mmol; from step (ii) above) and ethyl bromoacetate (95 mg; 0.57 mmol). Yield 8 mg (23%).

$^1$H-NMR:(500 MHz; CDCl$_3$) δ8.47 (bt, 1H), 7.83 (d, 2H), 7.48 (bs, 1H), 7.31 (d, 2H), 4.92 (dd, 1H), 4.85 (s, 2H), 4.58–4.39 (AB part of ABX spectrum, 2H), 4.16–4.06 (m, 4H), 3.24 (s, 2H), 4.87 (d, 1H), 2.65–2.59 (m, 1H), 2.56–2.48 (m, 1H), 2.10–0.95 (m, 16H)

EXAMPLE 58
MeOOC—C(=CEt)CH$_2$OOCCH$_2$—(R)Cgl-Aze-Pab-Z (i) MeOOC—C(=CH)C(OH)Et

Propionaldehyde (10.1 g; 0.174 mol) was added dropwise to a solution of methyl acrylate (10 g; 0.116mol) and 1,4-diazobicyclo[2,2,2]octane (1.3 g; 0.0116 mol). The reaction mixture was stirred at room temperature for 14 days. Ethyl acetate (150 ml) was added. The organic phase was washed with water and brine, dried (Na$_2$SO$_4$), filtered and concentrated to give the desired compound. Yield 15.5 g (93%).

$^1$H-NMR: (400 MHz; CDCl$_3$) δ6.24 (s, 1H), 5.81 (s, 1H), 4.34 (t, 1H), 3.78 (s, 3H), 2.82 (bs, 1H), 1.69 (m, 2H), 0.95 (t, 3H)

(ii) MeOOC—C(=CEt)CH$_2$Br

HBr (6.5 ml, ~48%) was added dropwise to MeOOC—C(=CH)C(OH)Et (3 g; 20.8 mmol; from step (i) above) at 0° C. After 5 minutes H$_2$SO$_4$ (conc.; 6 ml) was added dropwise. The reaction mixture was stirred for 12 hours at room temperature. Two phases was separated and the top phase was diluted with ether. The ether phase was washed with water and aqueous NaHCO$_3$, dried (Na$_2$SO$_4$ and charcoal) and concentrated. The 9 residue was purified by flash chromatography. Yield 1.7 g (40%).

$^1$H-NMR: (400 MHz; CDCl$_3$) δ6.97 (t, 3H), 4.23 (s, 2H), 3.8 (s, 3H), 2.32 (m, 2H), 1.13 (t, 3H)

(iii) tBuOOCCH$_2$—(R)Cgl-Aze-Pab-Z

The sub-title compound was prepared analogously to the procedure described in Example (iii) from H—(R)Cgl-Aze-Pab-Z (2.1 g; 3.6 mmol) and t-butyl bromoacetate (780 mg; 4.0 mmol). Yield 1.73 g (78%).

(iv) HOOCCH$_2$—(R)Cgl-Aze-Pab-Z

A solution of tBuOOCCH$_2$—(R)Cgl-Aze-PabZ (from step (iii) above) and TFA in methylene chloride was stirred in room temperature for 3 h. The rection mixture was concentrated and freeze dried from water and HCl (conc.; 10 eq.).

(v) MeOOC—C(=CEt)CH$_2$OOCCH$_2$—(R)Cgl-Aze-Pab-Z

A solution of HOOCCH$_2$—(R)Cgl-Aze-Pab-Z (263 mg; 0.41 mmol; from step (iv) above), NaOH (1M; 1.239 ml; 1.239 mmol) and water (4 ml) was freeze dried. DMF (5 ml) was added, followed by dropwise addition of Me—OOC—C(=CEt)CH$_2$Br (103 mg; 0.496 mmol; from step (ii) above) at 0° C. The reaction mixture was stirred for 24 h at room temperature, diluted with toluene (5 ml), washed with water, dried (Na$_2$SO$_4$) and concentrated. The residue was purified by flash chromatography using EtOAc:methanol (95:5) as eluent. Yield 95 mg (33%).

FAB-MS:(m+1)=690 (m/z)

EXAMPLE 59
MenOOCCH$_2$—(R)Cgl-Aze-Pab-COOPh(4-OMe)

(i) MenOOCCH$_2$Br

The sub-title compound was prepared analogously to the procedure described in Example 30(i) above from MenOH (10 mmol) and bromoacetyl chloride (12 mmol). Yield 1.5 g (54%).

(ii) MenOOCCH$_2$—(R)Cgl-Aze-Pab-COOPh(4-OMe)

The title compound was prepared analogously to the procedure described in Example 1(iii) from H—(R)Cgl-Aze-Pab-COO-Ph(4-OMe) (521 mg; 1 mmol; see Example 40(ii) above) and MenOOCCH$_2$Br (416 mg; 1.5 mmol; from step (i) above).Yield 36 mg (5%).

FAB-MS:(m+1)=718 (m/z)

EXAMPLE 60
tBuOOCCH$_2$—(R)Cgl-Aze-Pab-COOnPr

The title compound was prepared analogously to the procedure described in Example 1(iii) from H—(R)Cgl-Aze-Pab-COO-nPr (575 mg; 0.837 mmol; see Example 5(ii) above) and t-butyl bromoacetate (196 mg; 1.01 mmol). Yield 110 mg (23%).

LC-MS:(m+1)=572 (m/z)

EXAMPLE 61
MenOOCCH$_2$—(R)Cgl-Aze-Pab-Z

The title compound was prepared analogously to the procedure described in Example 1(iii) from H—(R)Cgl-Aze-Pab-Z (0.7 g; 1.21 mmol) and MenOOCCH$_2$Br (0.4 g; 1.45 mmol; see Example 59(i) above). Yield 0.33 g (38%).

FAB-MS:(m+1)=702 (m/z)

EXAMPLE 62
BnOOCCH$_2$—(R)Cgl-Aze-Pab-COO-Bn(4-NO$_2$)

(i) Boc-(R)Cgl-Aze-Pab-COO-Bn(4-NO$_2$)

The sub-title compound was prepared analogously to the procedure described in Example 1(i) from Boc-(R)Cgl-Aze-Pab-H (1.03 g; 2.18 mmol), 2M NaOH (24 mL) and 4-NO$_2$-benzyl chloroformate (518 mg; 2.4 mmol). Yield 1.32 g (93%).

FAB-MS:(m+1)=651(m/z)

(ii) H—(R)Cgl-Aze-Pab-COO-Bn(4-NO$_2$)

The sub-title compound was prepared analogously to the procedure described in Example 4(ii) from Boc-(R)Cgl-Aze-Pab-COO-Bn(4-NO$_2$) (1.32 mg; 2.03 mmol; from step (i) above). Yield 1.0 g (79%).

FAB-MS:(m+1)=551(m/z)

(iii) BnOOCCH$_2$—(R)Cgl-Aze-Pab-COO-Bn(4-NO$_2$)

The title compound was prepared analogously to the procedure described in Example 1(iii) from H—(R)Cgl-Aze-Pab-COO-Bn(4-NO$_2$) (0.5 g; 0.80 mmol; from step (ii) above) and benzyl bromoacetate (220 mg; 0.90 mmol).

FAB-MS: (m+1)=699(m/z)

EXAMPLE 63
EtOOCCH$_2$—(R)Cgl-Aze-Pab-Bn(4-NO$_2$)

The title compound was prepared analogously to the procedure described in Example 1(iii) from H—(R)Cgl-Aze-Pab-COO-Bn(4-NO$_2$) (211 mg; 0.38 mmol; see Example 62(ii) above) and ethyl bromoacetate (47 μl; 0.42 mmol). Yield 44 mg (18%).

$^1$H-NMR: (300 MHz; CDCl3) δ9.55 (bs, 1H), 8.50 (bt, 1H), 8.20 (d, 2H), 7.80 (d, 2H), 7.60 (d, 2H), 7.35 (d, 2H), 6.87 (bs, 1H), 4.95 (dd, 1H), 4.65–4.40 (AB part of ABX spectrum, 2H), 4.18–4.04 (m, 5H), 3.27–3.15 (AB-spectrum, 2H), 2.87 (d, 1H), 2.75–2.60 (m, 1H), 2.57–2.45 (m, 1H), 2.00–0.95 (m, 16H).

EXAMPLE 64
PrlC(O)CH$_2$OOCCH$_2$—(R)Cgl-Aze-Pab-Z (i) PrlC(O)CH$_2$OH

A mixture of 2,5-dioxo-1,4-dioxane (2.0 g; 17 mmol) and pyrrolidine (8 ml; 97 mmol) was refluxed for 1 h. The excess pyrrolidine was removed by evaporation. Yield 4.4 g (99%).

FAB-MS(m+1)=130(m/z)

(ii) PrlC(O)CH$_2$OOCCH$_2$Br

To a solution of PrlC(O)CH$_2$OH (0.4 g; 3.1 mmol; from step (i) above) in DMF (15 ml) was added dropwise bromoacetyl bromide (0.63 g; 3.1 mmol) at 0° C. The reaction mixture was stirred for 1.5 h at 0° C. and 3 h at room temperature. Additional bromoacetyl bromide (0.63 g; 3.1 mmol) was added and the reaction mixture was heated to 80° C., stirred at room temperature for 12 h and concentrated. Yield 320 mg (41%)

FAB-MS(m+1)=252(m/z)

(iii) PrlC(O)CH$_2$OOCCH$_2$—(R)CgI-Aze-Pab-Z

The title compound was prepared analogously to the procedure described in Example 1(iii) from H—(R)Cgl-Aze-Pab-Z (580 mg; 1 mmol) and PrlC(O)CH$_2$OOCCH$_2$Br (300 mg; 1.2 mmol; from step (ii) above). Yield 400 mg (60%).

FAB-MS(m+1)=675 (m/z)

$^1$H-NMR: (500 MHz; CDCl3) δ9.66–9.42 (bs, 1H), 8.64–8.56 (m, 1H), 8.03–7.93 (d, 2H), 7.89–7.66 (bs, 1H), 7.45 (d, 2H), 7.45–7.25 (m, 5H), 5.20 (s, 2H), 4.98–4.92 (dd, 1H), 4.82–4.74 (m, 1H), 4.62, 4.58 (AB spectrum, 2H), 4.26–4.05 (m, 3H), 3.47–3.16 (m, 6H), 2.95 (d, 1H), 2.78–2.68 (m, 1H), 2.54–2.42 (m, 1H), 2.03–1.95 (m, 16H)

EXAMPLE 65
(2-Me)BnOOCCH$_2$—(R)Cgl-Aze-Pab-COO-Bn(4-NO$_2$)

The title compound was prepared analogously to the procedure described in Example 1(iii) from H—(R)Cgl-Aze-Pab-COO-Bn(4-NO$_2$) (500 mg; 0.80 mmol; see Example 62(ii) above) and 2-(methyl)benzyl bromoacetate (234 mg; 0.96 mmol; see Example 32(i) above). Yield 528 mg (92%).

$^1$H-NMR: (400 MHz, CDCl$_3$) δ9.34 (bs, 1H), 8.38 (t, 1H), 8.09 (d, 2H), 7.72 (d, 2H), 7.48 (d, 2H), 7.37 (bs, 1H), 7.23 (d, 2H), 7.17–7.05 (m, 4H), 5.18 (s, 2H), 5.00 (s, 2H), 4.81 (dd, 1H), 4.45–4.34 (AB part of ABX spectrum, 2H), 4.04–3.97 (q, 1H), 3.93–3.86 (q, 1H), 3.27–3.17 (AB spectrum, 2H), 2.79 (d, 1H), 2.54–2.35 (m,2H), 2.22 (s, 3H), 1.91–1.84 (bd, 1H),1.71–1.39 (m, 5H),1.19–0.84 (m, 4H).

EXAMPLE 66
MeOOCCH$_2$—(R)Cgl-Aze-Pab-COOEt

The title compound was prepared analogously to the procedure described in Example 1(iii) from H—(R)Cgl-Aze-Pab-COOEt (305 mg; 0.69 mmol; see Example 4(ii) and methyl bromoacetate (126 mg; 0.83 mmol). Yield 188 mg (53%).

LC-MS:(m+1)=516(m/z)

EXAMPLE 67
(nPr)$_2$NC(O)CH$_2$OOCCH$_2$—(R)Cgl-Aze-Pab-COO-Bn(4-NO$_2$)

(i) (nPr)$_2$NC(O)CH$_2$Cl

A mixture of (nPr)$_2$NC(O)CH$_2$OH (244 mg; 1.53 mmol; see Example 12(i) above) and bromacetyl chloride (270 mg; 1.72 mmol) was stirred at room temperature for 12 hours. The mixture was poured into aqueous NaHCO$_3$ and extracted with methylene chloride. The organic phase was washed with aqueous KHSO$_4$ (0.2M) and brine, dried and concentrated.

FAB-MS:(m+1)=237(m/z)

$^1$H-NMR: (400 MHz, CDCl$_3$) δ4.82 (s, 2H), 4.22 (s, 2H), 3.31–3.26 (t, 2H), 3.10–3.15 (t, 2H), 1.68–1.52 (m, 2H), 1.97–0.86 (m, 6H)

(ii) (nPr)$_2$NC(O)CH$_2$OOCCH$_2$—(R)Cgl-Aze-Pab-COO-Bn (4-NO$_2$)

The title compound was prepared analogously to the procedure described in Example 1(iii) from H—(R)Cgl-Aze-Pab-COOBn(4-NO$_2$) (343 mg; 0.62 mmol; see Example 62(ii) above) and (nPr)$_2$NC(O)CH$_2$OOCCH$_2$Cl (160 mg; 0.68 mmol; from step (i) above). Yield 89 mg (19%).

FAB-MS:(m+1)=750(m/z)

EXAMPLE 68
(2-Me)BnOOCCH$_2$—(R)Cgl-Aze-Pab-COOCH$_2$OOCtBu

The title compound was prepared analogously to the procedure described in Example 1(iii) from H—(R)Cgl- Aze-Pab-COOCH$_2$OOCtBu (380 mg; 0.71 mmol; see Example 12(v) above) and 2-(methyl)benzyl bromoacetate (215 mg; 0.88 mmol; see Example 32(i) above). Yield 37 mg (7.5%).

FAB-MS:(m+1)=692(m/z)

EXAMPLE 69

The compounds of Examples 1 to 68 were all tested in Test A above and were all found to exhibit an IC$_{50}$TT value of more than 1.0 μM (ie they were are inactive to thrombin per se; cf. the active inhibitor HOOC—CH$_2$—(R)Cgl-Aze-Pab-H which exhibits an IC$_{50}$TT of 0.01 μM).

EXAMPLE 70

The compounds of Examples 1 to 68 were tested in one, two or all of Tests B, C and/or D above, and were all found to exhibit oral and/or parenteral bioavailability in the rat as the active inhibitor HOOC—CH$_2$—(R)Cgl-Aze-Pab-H, either as the free acid and/or as one or more ester thereof. Based on the assumption that HOOC—CH$_2$—(R)Cgl-Aze-Pab-H is formed in the rat, the bioavailability was calculated according to the formulae described in Test B and/or Test C as appropriate.

Abbreviations

| | |
|---|---|
| Ac = | acetyl |
| aq = | aqueous |
| Aze = | S-Azetidine-2-carboxylic acid |
| Boc = | t-butyloxycarbonyl |
| (Boc)$_2$O = | di-t-butyldicarbonate |
| Bn = | benzyl |
| Bu = | butyl |
| Cgl = | cyclohexylglycine |
| Ch = | cyclohexyl |
| DCC = | dicyclohexyl carbodiimide |
| DMAP = | N,N-dimethyl amino pyridine |
| EDC = | 1-(3-dimethylaminopropyl)-3-ethylcarbodiimide hydrochloride |
| Et = | ethyl |
| EtOH = | ethanol |
| EtOAc = | ethyl acetate |
| h = | hours |
| HCl = | hydrochloric acid |
| H-Pab-H = | 1-amidino-4-aminomethyl benzene |
| H-Pab-Z = | 4-aminomethyl-1-(N-benzyloxycarbonylamidino) benzene |
| HPLC = | high performance liquid chromatography |
| K$_2$CO$_3$ = | anhydrous potassium carbonate |
| Me = | methyl |
| Men = | (1R,2S,5R)-menthyl |
| Pab-OH = | 4-aminomethyl benzamidoxime (4-aminomethyl-1-(amino-hydroxyiminomethyl) benzene |
| Piv(aloyl) = | 2,2-dimethylacetyl |
| Pr = | propyl |
| Prl = | N-pyrrolidinyl |
| RPLC = | reverse phase high performance liquid chromatography |
| TFA = | trifluoroacetic acid |
| THF = | tetrahydrofuran |
| Z = | benzyloxy carbonyl |

Prefixes n, s, i and t have their usual meanings: normal, iso, sec and tertiary. Prefixes in the NMR-spectra s, d, t, q, and b mean singlet, doublet, triplet, quartet, and broad, respectively. The stereochemistry for the amino acids is by default (S) if not otherwise stated.

What is claimed is:

1. A compound of the formula I,

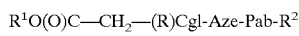   I wherein

R$^1$ represents H or C$_{1\text{-}10}$ alkyl;

R$^2$, which replaces one of the hydrogen atoms in the amidino unit of Pab-H, represents OH;

or a pharmaceutically-acceptable salt thereof.

2. MeOOCCH$_2$—(R)Cgl-Aze-Pab-OH.
3. EtOOCCH$_2$—(R)Cgl-Aze-Pab-OH.
4. nPrOOCCH$_2$—(R)Cgl-Aze-Pab-OH.
5. iPrOOCCH$_2$—(R)Cgl-Aze-Pab-OH.
6. tBuOOCCH$_2$—(R)Cgl-Aze-Pab-OH.
7. HOOCCH$_2$—(R)Cgl-Aze-Pab-OH.
8. A pharmaceutical formulation including a compound of formula I as defined in claim 1, or a pharmaceutically acceptable salt thereof, in admixture with a pharmaceutically acceptable adjuvant, diluent or carrier.
9. A pharmaceutical formulation including a compound of formula I as defined in claim 2, or a pharmaceutically acceptable salt thereof, in admixture with a pharmaceutically acceptable adjuvant, diluent or carrier.
10. A pharmaceutical formulation including a compound of formula I as defined in claim 3, or a pharmaceutically acceptable salt thereof, in admixture with a pharmaceutically acceptable adjuvant, diluent or carrier.
11. A pharmaceutical formulation including a compound of formula I as defined in claim 4, or a pharmaceutically acceptable salt thereof, in admixture with a pharmaceutically acceptable adjuvant, diluent or carrier.
12. A pharmaceutical formulation including a compound of formula I as defined in claim 5, or a pharmaceutically acceptable salt thereof, in admixture with a pharmaceutically acceptable adjuvant, diluent or carrier.
13. A pharmaceutical formulation including a compound of formula I as defined in claim 6, or a pharmaceutically acceptable salt thereof, in admixture with a pharmaceutically acceptable adjuvant, diluent or carrier.
14. A pharmaceutical formulation including a compound of formula I as defined in claim 7, or a pharmaceutically acceptable salt thereof, in admixture with a pharmaceutically acceptable adjuvant, diluent or carrier.
15. A method of treatment of a condition where inhibition of thrombin is required which method comprises the step of administering a therapeutically effective amount of a compound of formula I as defined in claim 1, or a pharmaceutically-acceptable salt thereof, to a person suffering from, or susceptible to, such a condition.
16. A method as claimed in claim 15, wherein the condition is thrombosis.
17. A method as claimed in claim 15, wherein the condition is hypercoagulability in blood and tissues.
18. A method of treatment of a condition where inhibition of thrombin is required which method comprises the step of administering a therapeutically effective amount of a formulation as defined in claim 8 to a person suffering from, or susceptible to, such a condition.
19. A method as claimed in claim 18, wherein the condition is thrombosis.
20. A method as claimed in claim 18, wherein the condition is hypercoagulability in blood and tissues.
21. A method of treatment of a condition where inhibition of thrombin is required which method comprises the step of administering a therapeutically effective amount of a compound of formula I as defined in claim 5, or a pharmaceutically-acceptable salt thereof, to a person suffering from, or susceptible to, such a condition.
22. A method as claimed in claim 21, wherein the condition is thrombosis.
23. A method as claimed in claim 21, wherein the condition is hypercoagulability in blood and tissues.
24. A method of treatment of a condition where inhibition of thrombin is required which method comprises the step of administering a therapeutically effective amount of a compound of formula I as defined in claim 3, or a pharmaceutically-acceptable salt thereof, to a person suffering from, or susceptible to, such a condition.

25. A method as claimed in claim 24, wherein the condition is thrombosis.

26. A method as claimed in claim 24, wherein the condition is hypercoagulability in blood and tissues.

27. A method of treatment of a condition where inhibition of thrombin is required which method comprises the step of administering a therapeutically effective amount of a compound of formula I as defined in claim 4, or a pharmaceutically-acceptable salt thereof, to a person suffering from, or susceptible to, such a condition.

28. A method as claimed in claim 27, wherein the condition is thrombosis.

29. A method as claimed in claim 27, wherein the condition is hypercoagulability in blood and tissues.

30. A method of treatment of a condition where inhibition of thrombin is required which method comprises the step of administering a therapeutically effective amount of a compound of formula I as defined in claim 5, or a pharmaceutically-acceptable salt thereof, to a person suffering from, or susceptible to, such a condition.

31. A method as claimed in claim 30, wherein the condition is thrombosis.

32. A method as claimed in claim 30, wherein the condition is hypercoagulability in blood and tissues.

33. A method of treatment of a condition where inhibition of thrombin is required which method comprises the step of administering a therapeutically effective amount of a compound of formula I as defined in claim 6, or a pharmaceutically-acceptable salt thereof, to a person suffering from, or susceptible to, such a condition.

34. A method as claimed in claim 33, wherein the condition is thrombosis.

35. A method as claimed in claim 33, wherein the condition is hypercoagulability in blood and tissues.

36. A method of treatment of a condition where inhibition of thrombin is required which method comprises the step of administering a therapeutically effective amount of a compound of formula I as defined in claim 7, or a pharmaceutically-acceptable salt thereof, to a person suffering from, or susceptible to, such a condition.

37. A method as claimed in claim 36, wherein the condition is thrombosis.

38. A method as claimed in claim 36, wherein the condition is hypercoagulability in blood and tissues.

* * * * *

UNITED STATES PATENT AND TRADEMARK OFFICE
CERTIFICATE OF CORRECTION

PATENT NO. : 5,965,692
DATED : October 12, 1999
INVENTOR(S) : Gustafsson et al.

It is certified that error appears in the above-identified patent and that said Letters Patent is hereby corrected as shown below:

Claim 21, line 4, delete "5" and replace by --2--.

Signed and Sealed this

Sixteenth Day of May, 2000

Attest:

Q. TODD DICKINSON

*Attesting Officer*     *Director of Patents and Trademarks*

UNITED STATES PATENT AND TRADEMARK OFFICE
CERTIFICATE OF CORRECTION

PATENT NO.    : 5,965,692
DATED         : October 12, 1999
INVENTOR(S)   : Gustafsson et al.

It is certified that error appears in the above-identified patent and that said Letters Patent is hereby corrected as shown below:

Column 10,
Line 36, delete "pharmaceutical" and replace by -- pharmaceutically --.

Column 35,
Lines 47 to 48, delete "(4-aminomethyl-1-(amino-hydroxyiminomethyl) benzene" and replace by -- (4-aminomethyl-1-(amino-hydroxyiminomethyl) benzene) --.

Signed and Sealed this

Twenty-sixth Day of March, 2002

Attest:

*Attesting Officer*

JAMES E. ROGAN
*Director of the United States Patent and Trademark Office*